(12) United States Patent
Pal

(10) Patent No.: US 8,608,690 B2
(45) Date of Patent: Dec. 17, 2013

(54) MELT-BONDED JOINT FOR JOINING SHEATHS USED IN MEDICAL DEVICES, AND METHODS OF FORMING THE MELT-BONDED JOINT

(75) Inventor: Dharmendra Pal, Irvine, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/098,016

(22) Filed: Apr. 29, 2011

(65) Prior Publication Data

US 2011/0208164 A1    Aug. 25, 2011

Related U.S. Application Data

(62) Division of application No. 11/408,279, filed on Apr. 20, 2006, now Pat. No. 7,968,032.

(60) Provisional application No. 60/761,594, filed on Jan. 23, 2006, provisional application No. 60/673,199, filed on Apr. 20, 2005.

(51) Int. Cl.
 *A61M 25/00* (2006.01)
(52) U.S. Cl.
 USPC .................................... 604/103.04; 604/523
(58) Field of Classification Search
 USPC .......... 604/103, 103.04, 102.01, 103.06, 433, 604/434, 585, 164.13, 523; 606/191, 192, 606/194, 198; 623/1.27, 1.35; 600/433, 600/434, 585
 See application file for complete search history.

(56) References Cited

U.S. PATENT DOCUMENTS

| 4,580,568 A | 4/1986 | Gianturco |
| 5,035,706 A | 7/1991 | Gianturco et al. |
| 5,257,974 A | 11/1993 | Cox |
| 5,282,824 A | 2/1994 | Gianturco |

(Continued)

FOREIGN PATENT DOCUMENTS

| EP | 0 850 653 A2 | 7/1998 |
| EP | 1 004 327 A1 | 5/2000 |

(Continued)

OTHER PUBLICATIONS

PCT Notification of Transmittal of the International Search Report and the Written Opinion of the International Searching Authority, or the Declaration dated Aug. 30, 2006 for International Patent Application No. PCT/US2006/015149.

(Continued)

*Primary Examiner* — Brian E. Pellegrino
(74) *Attorney, Agent, or Firm* — Brinks Gilson & Lione

(57) ABSTRACT

Joint assemblies for joining sheaths for use in medical devices are provided, as are methods of manufacturing the joint assemblies. An elongate first sheath has a distal end portion having melt bonding material. A second sheath has first and second end portions, the second end portion having melt bonding material. An outer sleeve body includes proximal and distal engaging portions that have melt bonding materials. The proximal engaging portion is disposed about and melt bonded to the first sheath distal end portion. The distal engaging portion is disposed about and melt bonded to the second sheath proximal end portion. In one embodiment, one or both sheaths have an inner layer, a coiled middle layer optionally stopping short of the joint assembly, and an outer layer that has said melt bonding materials. In one embodiment, the sheaths are used in a rapid insertion catheter delivery system.

13 Claims, 19 Drawing Sheets

(56) References Cited

U.S. PATENT DOCUMENTS

| | | | |
|---|---|---|---|
| 5,380,304 | A | 1/1995 | Parker |
| 5,407,432 | A | 4/1995 | Solar |
| 5,507,771 | A | 4/1996 | Gianturco |
| 5,545,134 | A | 8/1996 | Hilaire et al. |
| 5,690,644 | A | 11/1997 | Yurek et al. |
| 5,700,253 | A | 12/1997 | Parker |
| 5,720,776 | A | 2/1998 | Chuter et al. |
| 5,743,874 | A * | 4/1998 | Fischell et al. ........... 604/103.04 |
| 5,743,875 | A | 4/1998 | Sirhan et al. |
| 5,823,995 | A | 10/1998 | Fitzmaurice et al. |
| 6,030,405 | A | 2/2000 | Zarbatany et al. |
| 6,063,318 | A | 5/2000 | Houser et al. |
| 6,143,013 | A * | 11/2000 | Samson et al. ................. 606/192 |
| 6,171,279 | B1 | 1/2001 | Hilaire et al. |
| 6,290,693 | B1 | 9/2001 | Jung, Jr. et al. |
| 6,299,635 | B1 | 10/2001 | Frantzen |
| 6,330,884 | B1 | 12/2001 | Kim |
| 6,380,457 | B1 | 4/2002 | Yurek et al. |
| 6,503,223 | B1 | 1/2003 | Sikido et al. |
| 6,589,227 | B2 | 7/2003 | Sønderskov Klint |
| 6,592,549 | B2 | 7/2003 | Gerdts et al. |
| 6,605,062 | B1 * | 8/2003 | Hurley et al. ........... 604/164.13 |
| 6,613,075 | B1 | 9/2003 | Healy et al. |
| 6,679,909 | B2 | 1/2004 | McIntosh et al. |
| 6,723,071 | B2 | 4/2004 | Gerdts et al. |
| 6,743,252 | B1 | 6/2004 | Bates et al. |
| 6,746,423 | B1 | 6/2004 | Wantink |
| 6,755,855 | B2 | 6/2004 | Yurek et al. |
| 6,837,870 | B2 | 1/2005 | Duchamp |
| 6,939,370 | B2 | 9/2005 | Hartley et al. |
| 7,273,485 | B2 | 9/2007 | Simpson et al. |
| 7,273,487 | B1 | 9/2007 | Duchamp et al. |
| 7,303,580 | B2 | 12/2007 | Parker |
| 7,578,838 | B2 | 8/2009 | Melsheimer |
| 7,691,139 | B2 | 4/2010 | Baker et al. |
| 2002/0007145 | A1 | 1/2002 | Stivland et al. |
| 2002/0082525 | A1 | 6/2002 | Oslund et al. |
| 2002/0165598 | A1 | 11/2002 | Wahr et al. |
| 2003/0109886 | A1 | 6/2003 | Keegan et al. |
| 2003/0125709 | A1 | 7/2003 | Eidenschink |
| 2003/0125751 | A1 | 7/2003 | Griffin et al. |
| 2003/0153942 | A1 | 8/2003 | Wang et al. |
| 2004/0015150 | A1 | 1/2004 | Zadno-Azizi |
| 2004/0116833 | A1 | 6/2004 | Kato et al. |
| 2004/0167601 | A1 | 8/2004 | Gerdts et al. |
| 2004/0186505 | A1 * | 9/2004 | Joergensen et al. ...... 604/103.04 |
| 2004/0199240 | A1 | 10/2004 | Dorn |
| 2004/0267280 | A1 | 12/2004 | Nishide et al. |
| 2004/0267563 | A1 | 12/2004 | Dunn et al. |
| 2005/0043756 | A1 | 2/2005 | Lavelle et al. |
| 2005/0113902 | A1 | 5/2005 | Geiser et al. |
| 2005/0171473 | A1 | 8/2005 | Gerdts et al. |
| 2006/0020321 | A1 | 1/2006 | Parker |
| 2006/0155357 | A1 | 7/2006 | Meisheimer |
| 2006/0212105 | A1 | 9/2006 | Dorn et al. |
| 2006/0282041 | A1 | 12/2006 | Meisheimer et al. |

FOREIGN PATENT DOCUMENTS

| | | |
|---|---|---|
| EP | 1 095 634 A1 | 5/2001 |
| WO | WO 00/24450 A1 | 5/2000 |
| WO | WO 03/003944 A2 | 1/2003 |
| WO | WO 03/003944 A3 | 1/2003 |

OTHER PUBLICATIONS

International Search Report and the Written Opinion of the International Searching Authority dated Aug. 3, 2007 for International Patent Application No. PCT/US2006/014864.

International Search Report and the Written Opinion of the International Searching Authority dated Apr. 11, 2007 for International Patent Application No. PCT/US2006/014870.

International Search Report and the Written Opinion of the International Searching Authority dated Mar. 16, 2007 for International Patent Application No. PCT/US2006/014874.

International Search Report and the Written Opinion of the International Searching Authority dated Apr. 11, 2007 for International Patent Application No. PCT/US2006/014875.

International Search Report and the Written Opinion of the International Searching Authority dated May 10, 2007 for International Patent Application No. PCT/US2006/015150.

Invitation to Pay additional Fees for PCT US/2006/014864, dated Apr. 13, 2007.

"Zilver® 518 Biliary—Stent," COOK®, 2005.

* cited by examiner

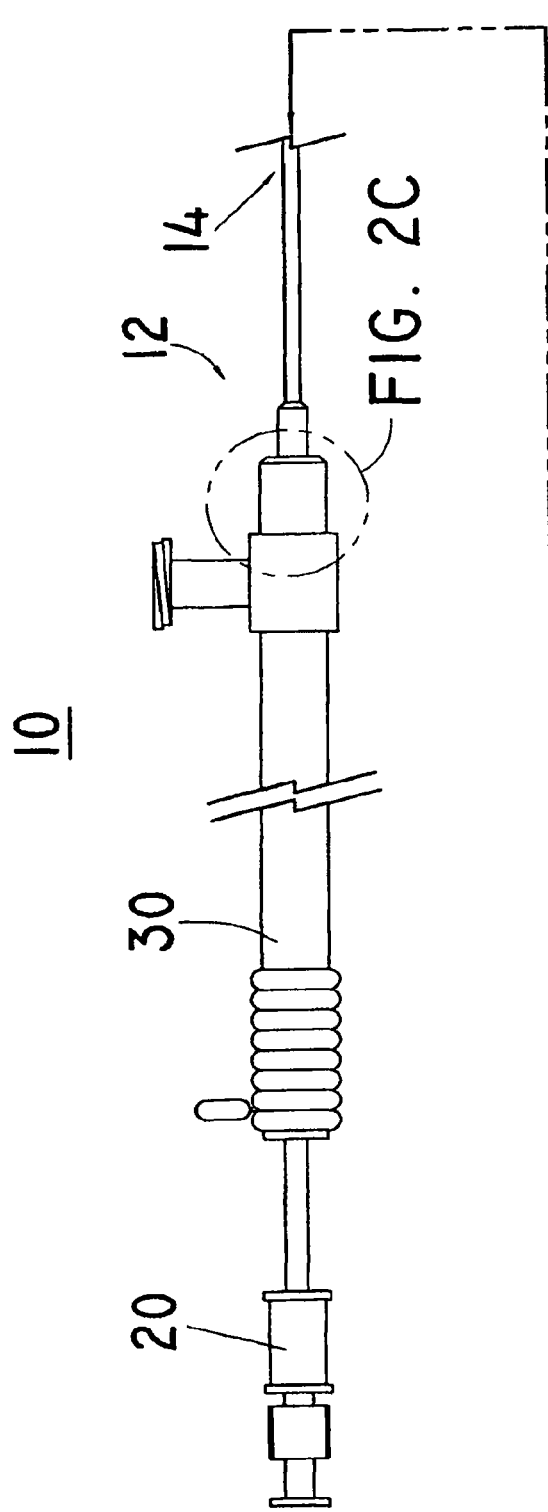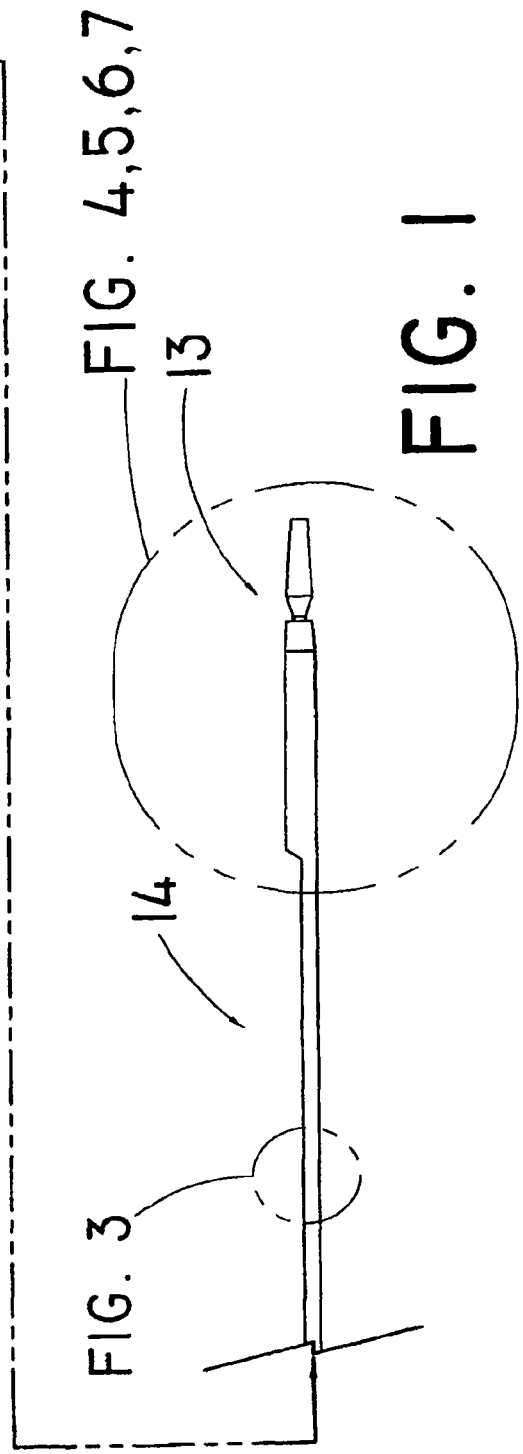

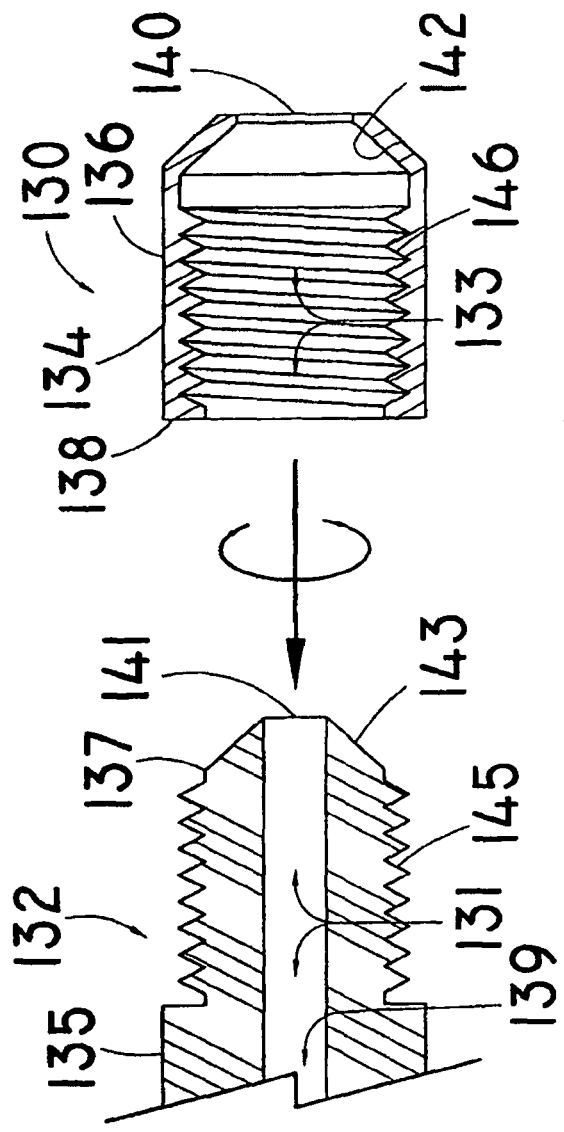
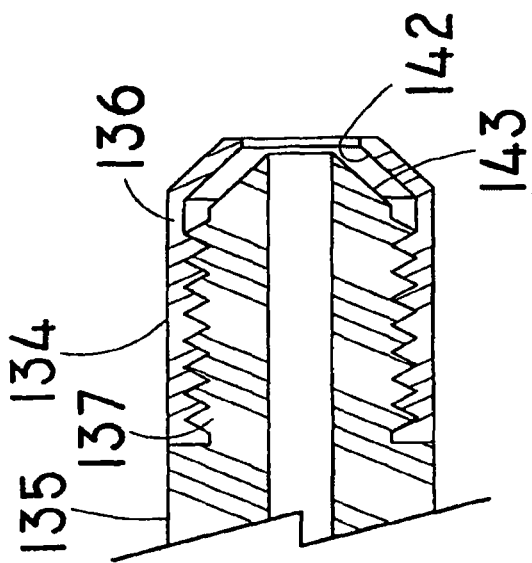
FIG. 2A
FIG. 2B

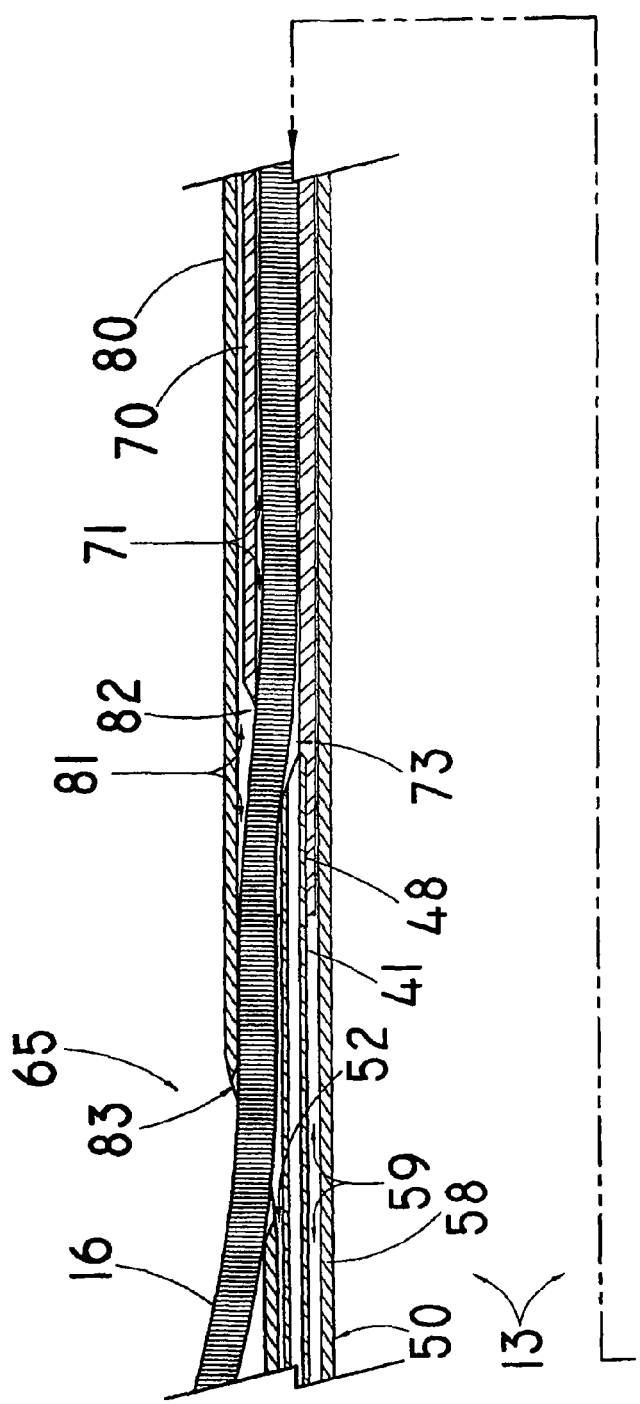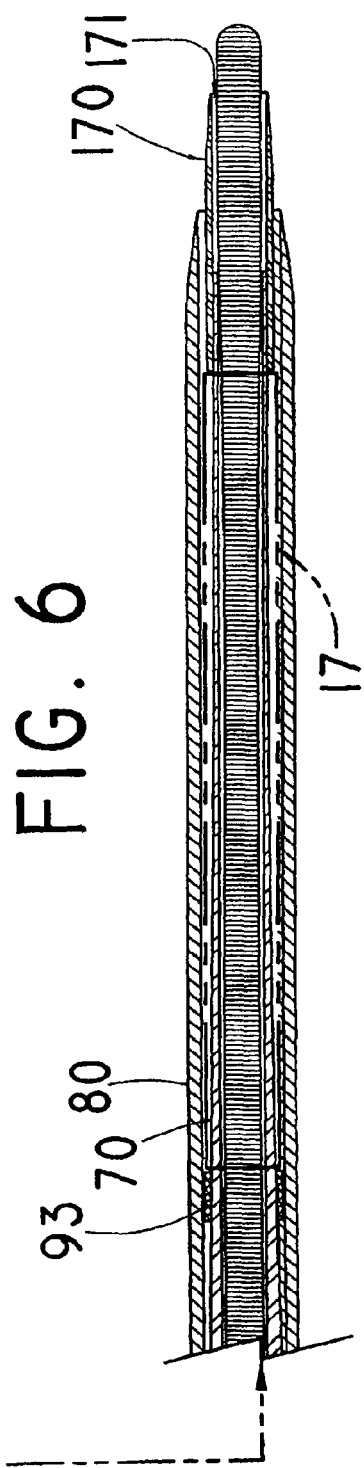
FIG. 6

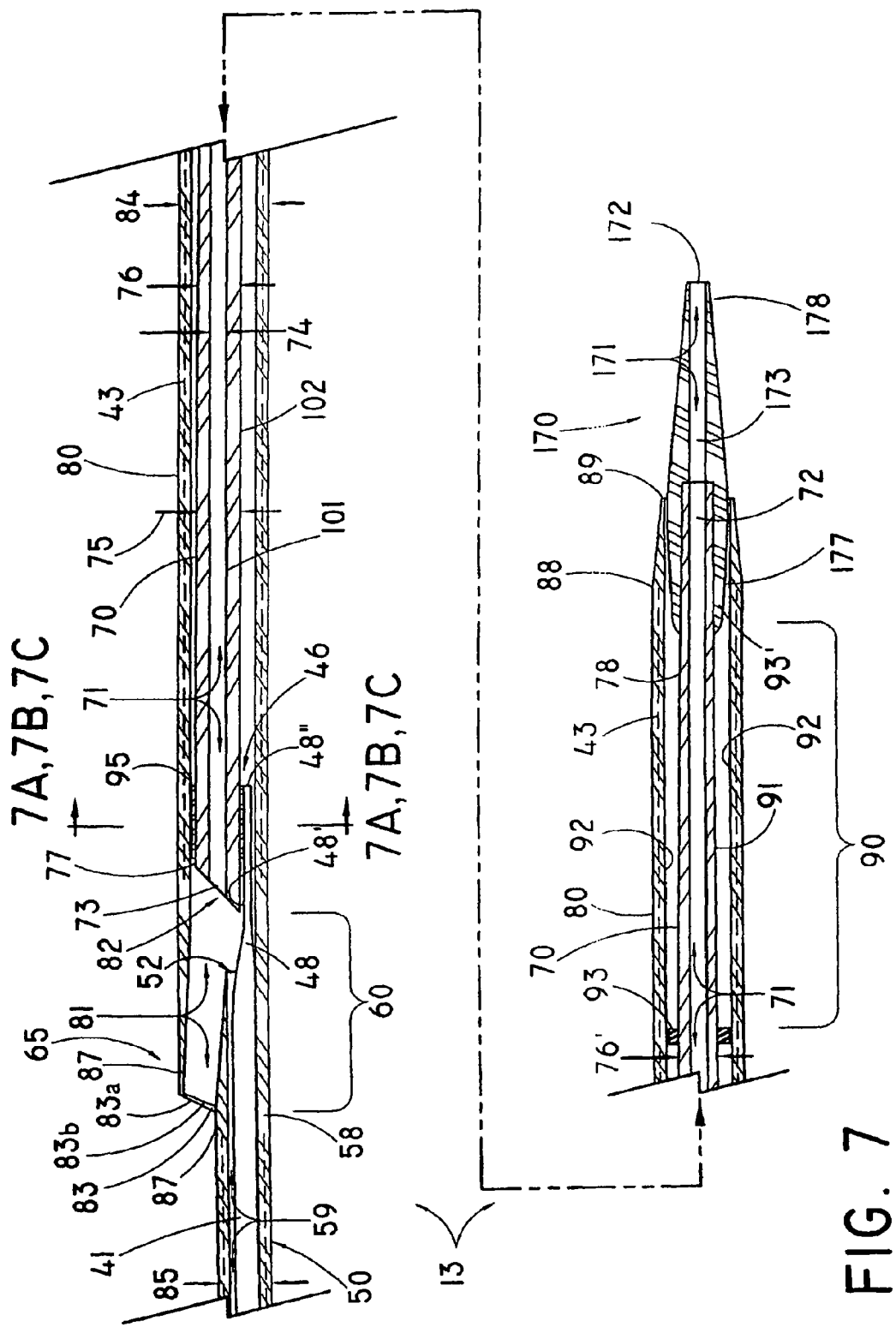

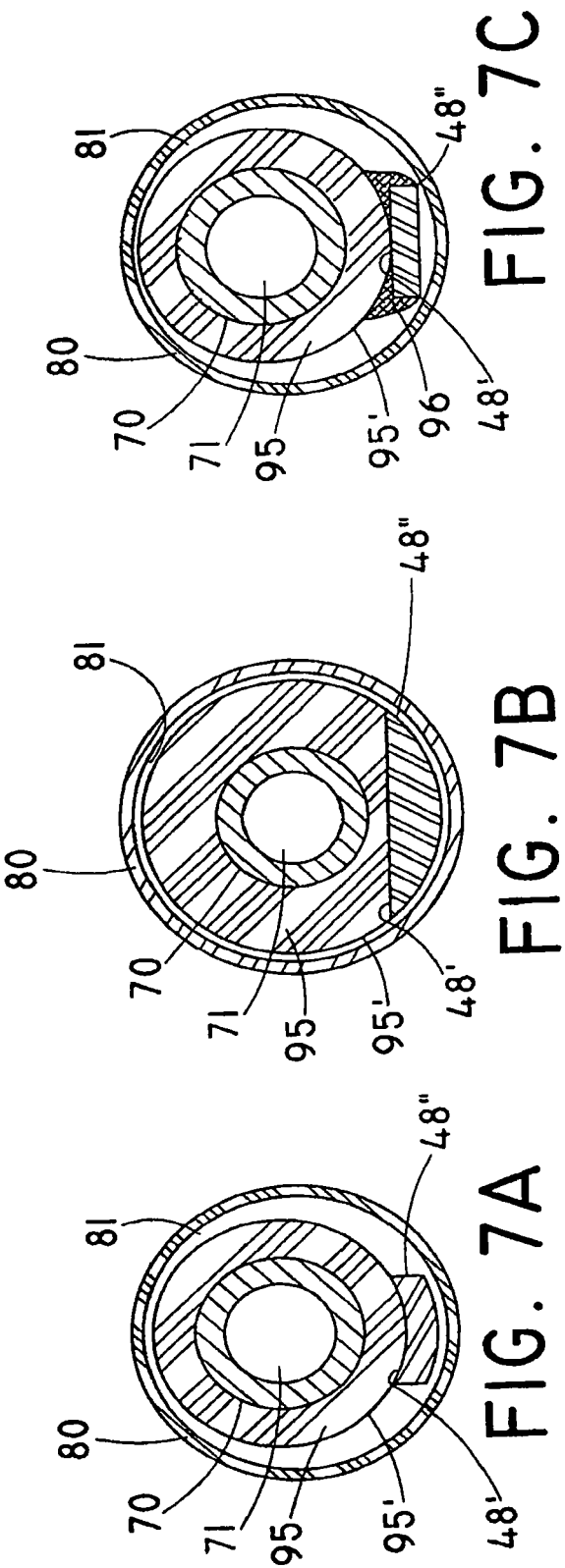

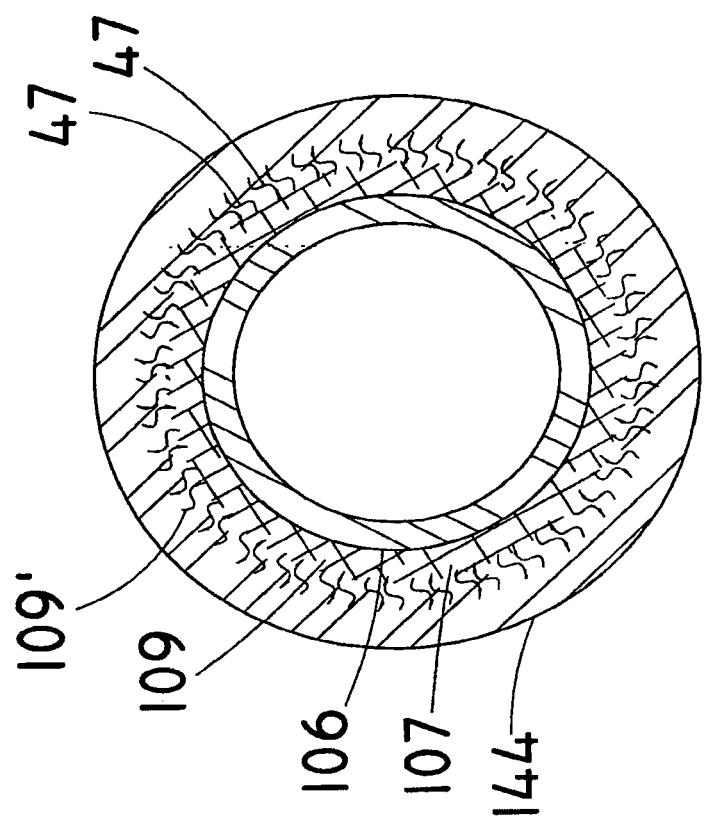
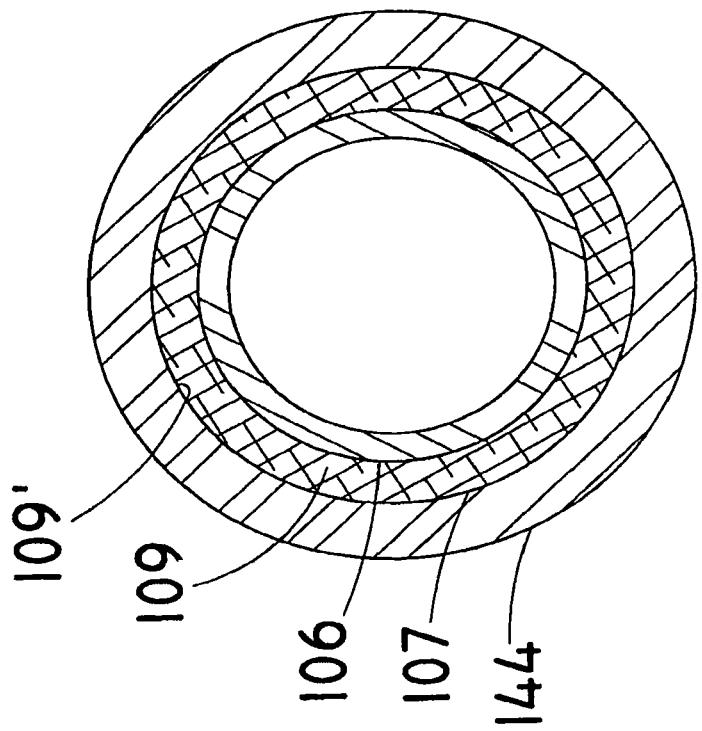
FIG. 8E
FIG. 8D

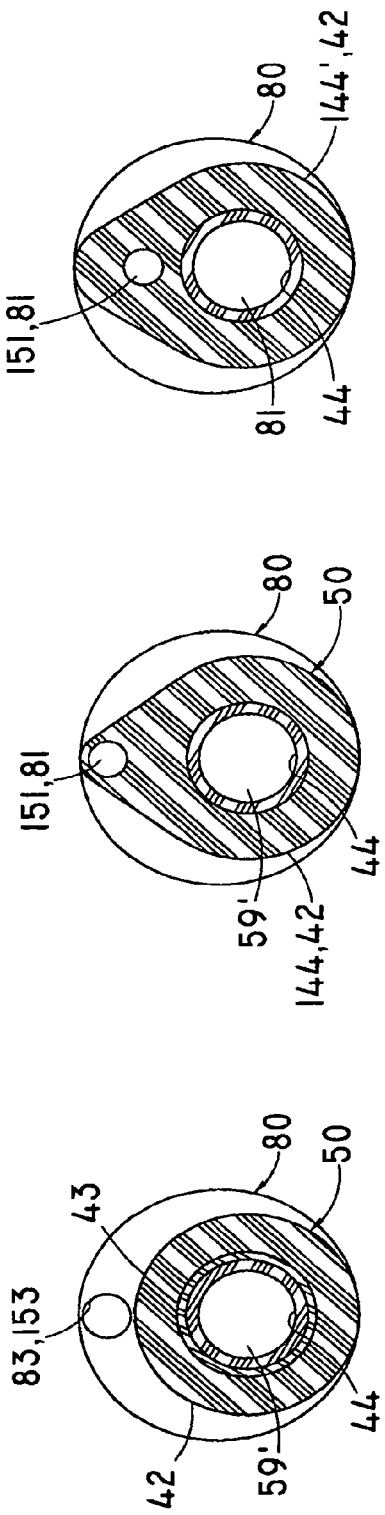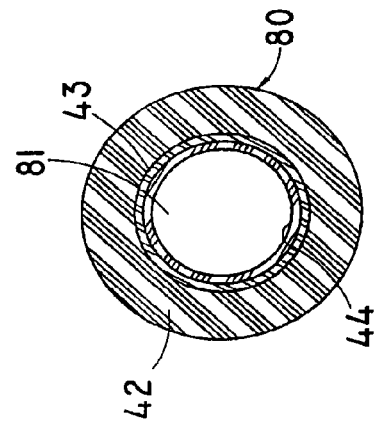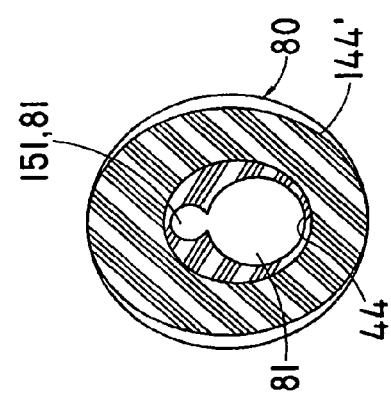

MELT-BONDED JOINT FOR JOINING SHEATHS USED IN MEDICAL DEVICES, AND METHODS OF FORMING THE MELT-BONDED JOINT

RELATED APPLICATIONS

The present patent document is a division of U.S. patent application Ser. No. 11/408,279, which was filed on Apr. 20, 2006, and which claims the benefit of the filing date under 35 U.S.C. §119(e) of U.S. Provisional Patent Application Ser. No. 60/761,594, filed on Jan. 23, 2006, and which also claims the benefit of the filing date under 35 U.S.C. §119(e) of U.S. Provisional Patent Application Ser. No. 60/663,034, filed on Apr. 20, 2005. All of the preceding patent documents are hereby incorporated by reference in their entireties.

FIELD OF THE INVENTION

The present invention relates to a joint for bonding sheaths, catheters, and tubular devices generally used percutaneously or through a delivery apparatus (such as an endoscope). In particular, the present invention relates to a melt-bonded joint, as well as methods of forming the melt-bonded joint, for joining bonding sheaths, catheters, and tubular devices for use with medical device delivery systems that deploy an implantable prosthesis such as self-expanding, balloon expandable, or non-expanding stents, prosthetic valve devices, and other implantable articles (individually and collectively, "stent," "stents," "implantable prosthesis," and "implantable prostheses") at a selected location inside a patient's body.

BACKGROUND OF THE INVENTION

This invention relates generally to medical device delivery systems and, in particular, to a joint for melt-bonding sheaths, catheters, and tubular devices (and methods of forming the melt-bonded joint) for medical device delivery systems that have a host of uses, including, for example, the deployment of a self-expanding implantable prosthesis at selected locations inside a patient's body. The invention may also be used, however, with a balloon expandable and non-expanding implantable prosthesis. In addition to being used with a rapid insertion delivery system, the invention may be used in an "over-the-wire" delivery system, so both systems will be described below.

By way of background, stents are configured to be implanted into body vessels having a passageway in order to reinforce, support, repair, or otherwise enhance the performance of the passageway. The term "passageway" is understood to be any lumen, channel, flow passage, duct, chamber, opening, bore, orifice, or cavity for the conveyance, regulation, flow, or movement of bodily fluids and/or gases of an animal. As an example, stents have been used in the passageways of an aorta, artery, bile duct, blood vessel, bronchiole, capillary, esophagus, fallopian tube, heart, intestine, trachea, ureter, urethra, vein, and other locations in a body (collectively, "vessel") to name a few.

One type of stent is self-expanding. For a self-expanding stent, the stent is resiliently compressed into a collapsed first, smaller diameter, carried by the delivery system, and due to its construction and material properties, the stent expands to its second, larger diameter upon deployment. In its expanded configuration, the stent exhibits sufficient stiffness so that it will remain substantially expanded and exert a radially outward force in the vessel passageway on an interior surface of the vessel. One particularly useful self-expanding stent is the Z-stent, introduced by Cook Incorporated, due to its ease of manufacturing, high radial force, and self-expanding properties. Examples of the Z-stent are found in U.S. Pat. Nos. 4,580,568; 5,035,706; 5,282,824; 5,507,771; and 5,720,776, the disclosures of which are incorporated in their entirety. The Zilver stent, introduced by Cook Incorporated, is another particularly useful self-expanding stent due to its nitinol platform and use of the Z-stent design properties. Examples of the Zilver stent are found in U.S. Pat. Nos. 6,743,252 and 6,299,635, the disclosures of which are incorporated in their entirety.

Many delivery systems employ a tubular catheter, sheath, or other introducer (individually and collectively, "catheter") having first and second ends and comprising a lumen for receiving the wire guide. Optionally, these delivery systems may fit through a working channel within an endoscope or an external accessory channel device used with an endoscope.

Generally stated, these delivery systems may fall within two categories. The first category of delivery systems to have been used, and consequently the first to be discussed below, is commonly referred to as an "over-the-wire" catheter system. The other category of delivery systems is sometimes referred to as a "rapid exchange" catheter system. In either system, a wire guide is used to position the delivery system within a vessel passageway. The typical wire guide has proximal and distal ends. A physician inserts the distal end into the vessel passageway, advances, and maneuvers the wire guide until the distal end reaches its desired position within the vessel passageway.

In the "over-the-wire" catheter delivery system, a physician places the catheter over the wire guide, with the wire guide being received into a lumen that extends substantially through the entire length of the catheter. In this over-the-wire type of delivery system, the wire guide may be back-loaded or front-loaded into the catheter. In front-loading an over-the-wire catheter delivery system, the physician inserts the distal end of the wire guide into the catheter's lumen at or near the catheter's proximal end. In back-loading an over-the-wire catheter delivery system, the physician inserts a distal portion of the catheter over the proximal end of the wire guide. The back-loading technique is more common when the physician has already placed the wire guide into the patient, which is typically the case today. In either case of back-loading or front-loading an over-the-wire catheter delivery system, the proximal and distal portions of the catheter will generally envelop the length of the wire guide that lies between the catheter first and second ends. While the wire guide is held stationary, the physician may maneuver the catheter through the vessel passageway to a target site at which the physician is performing or intends to perform a treatment, diagnostic, or other medical procedure.

Unlike the over-the-wire system where the wire guide lies within the catheter lumen and extends substantially the entire length of the catheter, in a novel "rapid insertion" catheter delivery system described in application Ser. No. 60/663,034, the wire guide occupies a catheter lumen extending only through a distal segment of the catheter. The so-called rapid insertion system comprises a system proximal end, an elongate flexible middle section and a system distal end that is generally tubular.

The system distal end, in general, comprises an inner guide channel member sized to fit within an outer guide channel member that is substantially axially slideable relative to the inner guide channel member. The outer guide channel member and inner guide channel member further have entry and exit ports defining channels configured to receive a wire guide. A port includes any structure that functions as an entry or exit aperture, cutout, gap, hole, opening, orifice, passage, passageway, port, or portal, while a guide channel is understood to be any aperture, bore, cavity, chamber, channel, duct, flow passage, lumen, opening, orifice, or passageway that facilitates the conveyance, evacuation, flow, movement, passage, regulation, or ventilation of fluids, gases, or a diagnostic, monitoring, scope, other instrument, or more particularly a catheter or wire guide.

A wire guide may extend from the outer and inner member entry ports, through the outer and inner member guide channels, and exit the distal end at or near a breech position opening located at or near a transition region where the guide channels and exit ports are approximately aligned relatively coaxially to facilitate a smooth transition of the wire guide. Furthermore, the outer guide channel member has a slightly stepped profile, whereby the outer guide channel member comprises a first outer diameter and a second smaller outer diameter proximal to the first outer diameter and located at or near the transition region.

The system distal end also has a self-expanding deployment device mounting region (e.g., a stent mounting region) positioned intermediate the inner guide channel member entry and exit ports for releasably securing a stent. At the stent mounting region, a stent is releasably positioned axially intermediate distal and proximal restraint markers and sandwiched transversely (i.e., compressed) between the outside surface of the inner guide channel member and the inside surface of an outer guide channel member.

Turning to the system proximal end of the rapid insertion delivery system, the proximal end, in general, comprises a handle portion. The handle portion has a handle that the physician grips and a pusher stylet that passes through the handle. The pusher stylet is in communication with—directly or indirectly through intervening parts—the inner guide channel member at the distal end. Meanwhile, the handle is in communication with—directly or indirectly through intervening parts—the outer guide channel member at the distal end. Holding the pusher stylet relatively stationary (while, for example, actuating the handle) keeps the stent mounting region of the inner guide channel member properly positioned at the desired deployment site. At the same time, proximally retracting the handle results in a corresponding proximal movement of the outer guide channel member relative to the inner guide channel member to thereby expose and, ultimately, deploy the self-expanding stent from the stent mounting region. At times, a physician may need to deploy a second self-expanding stent by withdrawing the system from the proximal end of the wire guide. The physician may then reload the catheter with additional stents, and if that is not an option the physician may load another stent delivery system with an additional stent, onto the wire guide. Also, the physician may withdraw the stent delivery system altogether and replace the delivery system with a catheter or different medical device intended to be loaded onto the wire guide.

The delivery system in the rapid exchange delivery system further comprises an elongate flexible middle section delivery device extending intermediate the system proximal end and the system distal end. The middle section delivery device comprises an outer sheath and an inner compression member having first and second ends associated with the system distal end and system proximal end, respectively.

More particularly, the outer sheath first end may be coterminous with or, if separate from, may be associated with (e.g., joined or connected directly or indirectly) the distal end outer guide channel member at or near the transition region, while the outer sheath second end is associated with the handle at the system proximal end. The inner compression member first end is associated with the distal end inner guide channel member at or near the transition region, while the inner compression member second end is associated with the pusher stylet at the proximal end. Therefore, the outer guide channel member of the distal end may move axially (as described above) and independently relative to an approximately stationary inner guide channel member of the system distal end and, thereby, deploy the stent.

Before the novel "rapid exchange" catheter delivery system described in application Ser. No. 60/663,034 and the present invention, the ways of associating an outer sheath distal end and an outer guide channel member second end at a transition region has been to use glue, adhesives, and the like (collectively, "glue"), or to use a subassembly (or insert) that attaches at a proximal end to the outer sheath and attaches at a distal end to the outer guide channel member. One must choose the right glue, however, to join dissimilar materials, and glue must cure, thereby increasing the total processing (fixture) time in the application and assembly of the device. Furthermore, mating the subassembly to the outer sheath and outer guide channel member may be a time consuming and arduous task, one that requires preparation of a mold for a molding step. Moreover, subassemblies typically vary in strength and integrity depending on the joined materials having incongruous mating surfaces and, thereby, point attachments that could cause joint failure due to inadequate stress distribution. In addition, subassemblies typically are more rigid than the materials it joins, so the transition region is liable to kink and to not bend uniformly as the distal end of the outer body navigates a tortuous path within the vessel passageway.

The melt-bonded joint of the present invention solves these and other problems by joining the outer sheath distal end and the outer guide channel member second end at a transition region in a way that provides a breech position opening located at or near the second end of the outer member with a thermal mechanical melt bond that cures relatively fast and uniformly to distribute the stress across the entire bond and provide substantially uniform flexibility.

Therefore, it would be desirable to have a melt-bonded joint for joining sheaths for use with a delivery system for self-expanding devices such as stents, prosthetic valve devices, and other implantable articles inside a patient's body as taught herein, and methods of forming the melt-bonded joint.

SUMMARY OF THE INVENTION

The present invention provides a joint for joining sheaths for use in a medical device. In one embodiment, the present invention provides a device having a first sheath with a proximal end portion and a distal end portion defining a passageway therebetween, wherein the distal end portion has melt bonding material. A second sheath has a first end portion and a second end portion defining a channel therebetween, wherein the second end portion has melt bonding material. An outer sleeve body comprising melt-bonding material operatively couples to the first sheath distal end portion and to the second sheath second end portion.

Another embodiment provides a first sheath having an inner layer with a passageway extending longitudinally therethrough, a coil positioned longitudinally around at least a portion of the inner layer, and an outer layer disposed about the coil and being melt bonded to the inner layer through coil spacings. A second sheath having a first end portion and a second end portion and a channel therebetween is also provided. A joint operatively couples the first sheath distal end portion and the second sheath second end portion with melt bonding.

Methods of bonding sheaths for use in a medical device including, by way of example, a rapid insertion delivery system of self-expanding devices such as stents, prosthetic valve devices, and other implantable articles inside a patient's body a wire guide are also provided. In one embodiment, a first sheath having proximal and distal end portions and a passageway therebetween, and an outer surface at or near the distal end portion, is provided. A second sheath having first and second end portions and a channel therebetween, and an outer surface at or near the second end portion, is also provided. The first sheath distal end portion and the second sheath second end portion are conjoined, a first mandrel positioned in the first sheath passageway and the second sheath channel, and a second mandrel positioned along the first sheath outer surface and within the second sheath channel. A melt-bonding material is disposed about the first sheath distal end portion and the second sheath second end portion, and shrink-wrap material is disposed about the melt-bonding material. The melt-bonded material is melted, then cooled to a solid state to form a channeled joint for operatively coupling the first sheath distal end portion and the second sheath second end portion. The shrink-wrap material is removed.

BRIEF DESCRIPTION OF THE DRAWINGS

FIG. 1 is a schematic view, broken away, of a medical device system according to one embodiment of the invention.

FIG. 2A shows longitudinally sectioned exploded side views of a handle first connector and a handle second connector according to one embodiment of the invention.

FIG. 2B shows a longitudinally sectioned side view of operatively coupled first and second connectors according to FIG. 2A.

FIG. 6 is a longitudinally sectioned view of an embodiment of a distal end according to the invention, shown having a portion of a wire guide.

FIG. 7 is a longitudinally sectioned view, broken away, of another embodiment of a distal end of a medical device delivery system according to one embodiment of the invention.

FIGS. 7A, 7B, and 7C show cross sectional views of FIG. 7 taken along the lines 7A-7A, 7B-7B, and 7C-7C, respectively.

FIGS. 8B, 8C, 8D, and 8E show cross sectional views of FIG. 8A taken along the lines 8B-8B, 8C-8C, 8D-8D, and 8E-8E, respectively, where FIGS. 8B and 8D show components before melt bonding while FIGS. 8C and 8E show the components after melt bonding.

FIGS. 9A, 9B, 9C, 9D, and 9E are cross sectional views of FIG. 9 taken along the lines A-A, B-B, C-C, D-D, and E-E, respectively.

DETAILED DESCRIPTION OF EMBODIMENTS

Figure 2:
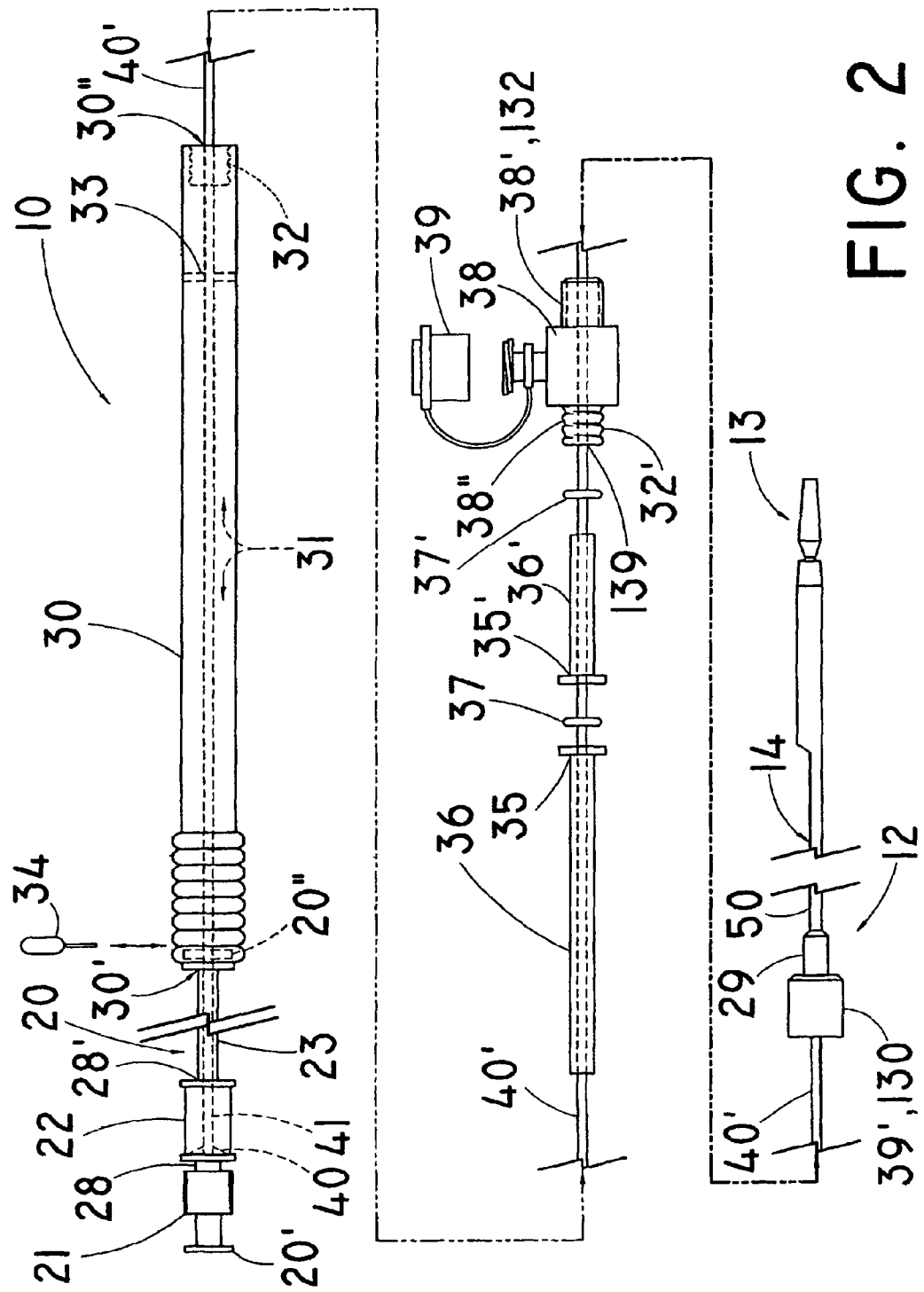
FIG. 2 is an exploded side view, broken away, of a proximal end of a medical device according to one embodiment of the invention.

The present invention relates to medical devices, and in particular to a melt-bonded joint for joining sheaths, catheters, tubular devices (individually and collectively, "sheath," "sheaths," and variants thereof). The present invention should not be limited to a medical device delivery system, and may be used for a variety of medical devices when two sheaths need joining. In one embodiment by way of example only and not by way of limitation, the present invention joins two sheaths for use in a delivery system configured for deploying expandable metallic, polymeric, and plastic devices or non-expanding metallic, polymeric, and plastic devices, which devices may include, by way of example and not by way of limitation, stents, prosthetic valve devices, and other implantable articles at selected locations inside a patient's body. For conciseness and ease of description of the embodiments of the invention, the term "stent" and its variations shall refer individually and collectively (without limiting the invention) to all self-expanding, balloon-expandable, or non-expanding devices used with the invention, such as stents, prosthetic valve devices, and other implantable articles inside a patient's body.

Against that backdrop and for the purposes of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, with, contain(s) and the variants thereof are intended to be open ended transitional phrases, terms, or words that do not preclude the possibility of additional steps or structure.

In FIG. 1, an illustrative embodiment of a delivery system 10 having a host of uses, including for the rapid insertion of self-expanding stents, is provided. The delivery system 10 comprises a system proximal portion 12, a middle section delivery device 14, and a system distal portion 13 shown in a partially deploying position.

System Proximal Portion 12

In the embodiment shown in FIG. 1, the proximal portion 12 remains outside of the patient's body. The proximal portion 12 comprises a handle 30 and an optional pusher stylet 20.

FIG. 1 depicts a schematic representation of the handle 30 and the optional pusher stylet 20 shown more particularly in FIG. 2. In general, a handle 30 retracts an outer guide channel member (discussed below) of the distal portion 13 of the delivery system 10 to deploy a stent, as will be explained later. The handle 30 may comprise any mechanical, electromechanical, pneumatic, or hydraulic handle configured in communication with—directly or indirectly through intervening parts—the distal portion's outer guide channel member. Communication would include, by way of illustration and not by way of limitation, a handle 30 that uses or is otherwise associated with, directly or indirectly, an elongated mechanical wire, rod, shaft, cable, sheath, pneumatic tube, or hydraulic pistons, cylinders and/or flow paths configured for moving the outer guide channel member proximally in order to deploy a stent.

FIG. 2 provides a schematic view, broken away, of a delivery system 10 for rapid insertion of self-expanding stents, but could be used with other implantable prostheses described above. The delivery system 10 shown in FIG. 2 is one embodiment of the proximal portion 12, middle section delivery device 14, and distal portion 13 shown in a partially deploying position. The middle section delivery device 14 extends distally from the proximal portion 12, and a distal portion 13 extends to a position that is distal the middle section delivery device 14. More particularly, FIG. 2 shows an exploded view of the proximal portion 12 of the delivery system 10 according to one embodiment of the invention, with an emphasis on the handle 30 and the optional stylet 20. Features of one embodiment of a handle 30 and pusher stylet 20 are discussed below.

The handle 30 comprises any tubular structure having a distal aperture 30" and a proximal aperture 30', the apertures defining a chamber 31 therebetween. In general, the handle 30 is a component, instrument, mechanism, tool, device, apparatus, or machine configured for directly or indirectly retracting an outer guide channel member (discussed below) of the distal portion 13 of the device to expose and, ultimately, to deploy a stent self-expanding implantable prostheses such as stents, prosthetic valve devices, and other implantable articles (hereafter, "stent" or "stents") at a selected location inside a patient's body.

The handle 30 is axially slideable relative to an elongate (long) inner compression member 41 that comprises a proximal end 40 and a middle section 40'. As discussed more fully below, the inner compression member 41 helps to keep the stent from moving proximally with proximal movement of the handle 30, which handle movement causes the outer guide channel member to withdraw proximally over the stent in order to expose and thereby to deploy the stent. Thus, the inner compression member helps to "push" the stent or stent carrying inner guide channel member in order to counter the urge for the stent or stent carrying member to prolapse proximally with the withdrawing of the outer guide channel member. As will be understood, "pushing" on the inner compression member will keep the stent carrying inner guide channel member (and therefore the stent) from translating as a result of an outer sheath or outer guide channel member being pulled over the stent; thereby "pushing" holds the stent in place at the desired deployment site within the patient's body. In one embodiment, the handle 30 is a unidirectional handle that is axially slideable relative to the inner compression member 41 and/or the optional pusher stylet 20 in order to deploy a stent. In one embodiment, the inner compression member 41 is secured to a pusher stylet 20.

As shown in FIG. 2, one embodiment of a pusher stylet 20 comprises a proximal end 20', a distal end 20", and a cannula 23 intermediate the proximal and distal ends 20', 20", respectively, and a receptacle 22. The cannula 23, as should be understood, comprises any suitable hollow plastic or metal tube. As a hollow tube, the cannula 23 optionally allows the inner compression member 41 to pass proximally through the cannula 23 and to the proximal end 20' so that the inner compression member proximal end 40 (such as a proximal end that is flared) may secure to a plug 21 that fits within the receptacle 22, wherein FIG. 2 shows the proximal end 20', plug 21, and an optional securing material 28 are shown in an exploded view relative to the receptacle 22 into which they may be secured. Furthermore, the cannula 23 assists with keeping that portion of the inner compression member substantially straight.

The stylet 20 is optional, because in an alternative embodiment the physician may hold the inner compression member proximal end 40' directly in order to "push" (e.g., hold substantially stationary) the stent carrying inner guide channel member (and therefore the stent). This controls the stent carrying inner guide channel member and stent from translating as a result of an outer sheath or outer guide channel member being pulled over the stent, so that the stent remains at the desired deployment site within the patient's body. Alternatively, the stylet 20 is any stationary handle secured to the inner compression member 41 for achieving the "pushing" (e.g., hold substantially stationary) of the stent or stent carrying inner guide channel member while the outer sheath or outer guide channel member are moved proximally.

The stylet distal end 20" is housed within the handle chamber 31 and is flared or otherwise flanged sufficiently to be larger than the handle proximal aperture 30' so as not to pull out of the chamber 31. In one embodiment, the stylet distal end 20" is secured to the distal portion of the stylet cannula 23, while in another embodiment the stylet distal end 20" is formed integral with the distal portion of the stylet cannula 23. Consequently, the stylet distal end 20" functions as a proximal stop that prevents the stylet cannula 23 from backing all the way out the handle while being axially slideable within the handle chamber 31. Thus, the stylet 20 will not slide off the handle 30, if so desired. The stylet distal end 20" may also, in one embodiment, function as a distal stop against a restraint 33 formed in the handle chamber 31 intermediate the handle proximal and distal apertures 30', 30", respectively, where intermediate should be understood to be any position between, and not necessarily equidistant to, the handle apertures 30', 30". As a result of the stylet distal end 20", the handle 30 may slide axially the distance separating the handle restraint 33 and the stylet distal end 20", which has a maximum distance of when the stylet distal end 20" is abutting the handle proximal aperture 30'.

A threaded tapered plug 21 and threaded tapered receptacle 22 optionally secure the inner compression member proximal end 40. In one embodiment, the inner compression member proximal end 40 is flared. Securing material 28, such as glue, adhesives, resins, welding, soldering, brazing, chemical bonding materials or combinations thereof and the like (collectively and individually, "glue") may be used to keep the threaded tapered plug 21 from backing out of the threaded tapered receptacle 22. A portion of the cannula 23 and stylet distal end 20" are received within the handle chamber 31 distal to the handle proximal aperture 30' as previously explained.

By optionally placing the inner compression member proximal end 40 in mechanical communication with the plug 21 and receptacle 22, the gripping and "pushing" (e.g., hold substantially stationary) on the stylet 20 (e.g., the receptacle 22) thereby helps to keep the inner compression member 41 from moving away from the distal portion 13 and, accordingly, counters the tendency for a stent or stent carrying member to move proximally during withdrawal of the outer guide channel member as will be explained below. Of course, the inner compression member may be secured elsewhere by the stylet 20, such as at or near the stylet distal end 20" or intermediate the stylet proximal and distal ends 20', 20", respectively, and the stylet distal end 20" may extend to a position at or near the distal end aperture 30" of the handle 30.

FIG. 2 shows a middle section 40' that extends distally from the proximal end 40 of the inner compression member 41. In one embodiment, the middle section 40' passes through the handle 30 (and may pass through the cannula 23 and/or bushings housed within the handle chamber 31 or other portions of the proximal portion 12). In one embodiment, the middle section 40' is elongate (at least 50.0 cm or longer as described below) and extends to a distance distally of the handle 30 and to a position at or near the medical system delivery device distal portion 13. It should be understood that, by describing the middle section 40' as passing through the handle 30, the middle section 40' does not necessarily need to pass proximally through the entire length of the handle 30, such as in an embodiment (by way of example and not by way of limitation) where the proximal end 40 of the inner compression member 41 is secured to a distal portion of the cannula 23 and/or the stylet distal end 20" extending within the handle chamber 31 to a position at or near the handle restraint 33.

In addition to holding a threaded tapered plug 21 and optionally the proximal end 40 of the inner compression member 41, the threaded tapered receptacle 22 may secure the proximal portion of the optional cannula 23. Glue 28' may be used at or near an interface of the cannula 23 and distal aperture of the threaded tapered receptacle 22. The glue 28' serves many functions, such as to keep dust from settling within the threaded tapered receptacle 22, to make the cannula 23 easier to clean, and to give aesthetics and a smooth feel to the device.

The handle 30 slidably receives the distal portion of the cannula 23 within the handle aperture 30' and handle chamber 31. As a result, the handle 30 is slidable relative to the stylet 20 (e.g., slidable relative to the threaded tapered plug 21, threaded tapered receptacle 22, and the cannula 23). In use, the physician grips the handle 30 in one hand and grips the stylet 20 (e.g., the receptacle 22) in the other hand. The physician holds the stylet 20 relatively stationary, which prevents the inner compression member and inner guide channel member and its stent carrying portion from moving proximally, and then withdraws the handle 30 proximally relative to the stationary stylet 20 and inner compression member 41. As a result, the physician is thereby retracting an outer guide channel member (discussed below) of the distal portion 13 of the delivery system 10 to expose and, ultimately, to deploy a stent locatable at the distal portion 13 of the delivery system 10. The handle 30 is in communication with—directly or indirectly through intervening parts—the outer guide channel member at the distal portion 13.

As shown in FIG. 2, some of those optional parts may include the following: a first bushing 36 having an optional first bushing flange 35; a second bushing 36' having an optional second bushing flange 35; an intermediate seal 37 intermediate the first and second bushing flanges 35, 35', respectively; a second seal 37' intermediate the second bushing flange 35' and a check flow body 38; and a detachable cap 39, such a Luer cap by way of example but not by way of limitation. In one embodiment, one or both of the intermediate seal 37 and the second seal 37' is from a class such as an O-ring. In another embodiment, one or both of the intermediate seal 37 and the second seal 37' is a cylinder or disk with a center aperture, and may be made from material that comprises an O-ring. The bushings 36, 36' are hollow plastic or metal tubes that take up space within the handle 30 so that the inner compression member has less room to buckle. Fully assembled in one embodiment, the first bushing 36 is inserted within the cannula 23 and the first bushing flange 35 is distal to and abutting the handle restraint 33, which is sized to interfere with the bushing flange 35 to prevent the bushing flange 35 from moving proximal to the handle restraint 33. The second bushing flange 35' is distal to and optionally abutting the bushing flange 35 so to prevent it from moving proximal the first bushing flange 35, and the second bushing 36' is inserted within an opening 139 of the check flow body 38. The intermediate seal 37 and the second seal 37' help to prevent fluids that could be used with the device (discussed below) from entering the handle chamber 31, which directs fluids distally, which fluids may be conveyed through an outer sheath 50 of the middle section delivery device 14 and system distal portion 13. In one embodiment, the handle restraint 33 is from a class such as a counterbore wherein the restraint 33 comprises, by way of example only and not by way of limitation, a flat-bottomed cylindrical enlargement of the handle chamber 31 sized for receiving a first bushing flange 35, an intermediate seal 37, a second bushing flange 35', and/or a check flow body proximal mating end 38" intermediate the restraint 33 and the handle distal aperture 30".

The handle 30 and check flow body 38 operatively couple with the handle distal aperture 30" receiving a check flow body proximal mating end 38" and being secured together by any suitable means, including but not limited to a crimp, friction fit, press fit, wedge, threading engagement, glue, adhesives, resins, welding (laser, spot, etc.), soldering, brazing, adhesives, chemical bonding materials, or combinations thereof. In one embodiment, the handle 30 comprises a coupling member 32 and the check flow body proximal mating end 38" comprises a coupling member 32', the coupling members 32, 32' being complementary to hold the handle 30 and check flow body proximal mating end 38" together. In one embodiment, the coupling members 32, 32' may form complementary threads. If it is desired to achieve quicker assembly for manufacturing purposes, then the coupling members 32, 32' may be an array of circumferential ridges that form an interference fit when pressed together. If a one-time snap fit is desired, then the coupling members 32, 32' may be circumferential ridges in the form of barbs. In another embodiment, the handle 30 and check flow body proximal mating end 38" may be put together and taken apart for servicing, in which case the coupling members 32, 32' may be circumferential ridges in the form of knuckle threads (e.g., circumferential ridges forming complementary undulating waves). The operatively coupled handle 30 and check flow body proximal mating end 38" according to these embodiments may be fixed such that they do not rotate relative to each other, or may rotate while preventing undesired axial separation.

During use, the detachable cap 39 may be detached or opened and the device flushed with saline to remove air in order to help keep air out of the patient. The intermediate seal 37 and the second seal 37' ensure that any flushed fluid moves distally in the device and does not back up into the handle 30, such as between the handle restraint 33 and the first bushing 36, into the handle chamber 31, or out the handle proximal aperture 30'. The detachable cap 39 (such as a Luer cap) keeps saline from backing out of the check flow body 38, air from flowing into the check flow body 38, and blood from rushing out during periods of high blood pressure inside the patient.

The medical device delivery systems 10 may be used to deploy an implantable prosthesis that is a balloon expandable or self-expanding stent, prosthetic valve device, or other implantable articles provided on the distal portion of a delivery system. In operation, a physician inserts the distal portion and at least a portion of the middle section delivery device into a vessel passageway, and advances them through the vessel passageway to the desired location adjacent the target site within the vessel passageway of a patient. In a subsequent step, the physician moves the handle proximally, which withdraws the outer sheath and/or the outer guide channel member and releasably exposes the stent for deployment. In another step, the physician inflates the expandable member, such as a balloon, positioned under the stent inner surface to plastically deform the stent into a substantially permanent expanded condition. The physician may inflate the expandable member by injecting fluid such as saline from a syringe into the inner compression member 41, via pusher stylet 20, through a Luer fitting at the proximal end 20'. Therefore, the fluid is directed distally to the expandable member, filling the expandable member chamber and expanding the stent. The physician then deflates the balloon and removes the catheter or delivery device from the patient's body.

In one embodiment as shown in FIG. 2, the handle 30 further comprises a check flow body distal mating end 38' and a connector cap 39' (optionally detachable) secured to the check flow body distal mating end 38', and a strain relief 29. In one embodiment, the connector cap 39' is from a class of fasteners such as nuts, and in one embodiment is a flare nut. The connector cap 39' functions to hold (or assist in holding in combination with the check flow body distal mating end 38') a flared proximal portion of an outer sheath 50 and/or a flared strain relief 29 disposed about (and optionally extending proximally from) that held portion of the outer sheath 50. The strain relief member 29 provides a kink resistant point where the outer sheath 50 connects to the connector cap 39' and/or the check flow body distal mating end 38'.

The check flow body distal mating end 38' and connector cap 39' may be operatively coupled mechanically, chemically, and/or chemical-mechanically. In one embodiment, the connector cap 39' is crimped, friction fitted, press fitted, and/or wedged into engagement onto the check flow body distal mating end 38'. In another embodiment for example, the check flow body distal mating end 38' and connector cap 39' are operatively coupled by glue, adhesives, resins, welding (laser, spot, etc.), soldering, brazing, adhesives, chemical bonding materials, or combinations thereof.

According to FIG. 2A, yet another embodiment of the connector cap 39' comprises a handle first connector 130 and the check flow body distal mating end 38' comprises a handle second connector 132. According to FIG. 2A, the handle first and second connectors 130, 132, respectively, function to operatively couple a strain relief member 29 operatively coupled to the proximal portion of the outer sheath 50 (discussed below). In one embodiment, the handle first connector 130 is from a class of fasteners such as nuts, and in one embodiment is a flare nut. Optionally, the distal portion of the second bushing 36' is sized (but for the second bushing flange 35') to be received within a check flow body proximal opening 139 in communication with the second connector 132.

FIG. 2A shows an exploded longitudinally sectioned side view of one embodiment of a portion of the handle comprising a first connector 130 and a second connector 132. The handle first connector 130 further comprises a proximal portion 134 and a distal portion 136. An opening 138 at the proximal portion 134 and an opening 140 at the distal portion 136 and define a lumen 133 therebetween. There is an engaging surface 142 at or near the distal portion 136. A threaded first piece 146 is disposed within the lumen 133 and intermediate the handle first connector distal end opening 140 and proximal end opening 138. The handle second connector 132 further comprises a proximal portion 135 and a distal portion 137. An opening 141 at the distal portion 137 and check flow body proximal opening 139 (e.g., FIG. 2) at the proximal portion 135 define a lumen 131 therebetween. There is an engaging surface 143 at or near the distal portion 137. A threaded second piece 145 is disposed on the outside surface and intermediate the handle second connector distal end opening 141 and the check flow body proximal opening 139.

According to one embodiment shown in FIGS. 2A and 2B, the second connector distal portion 137 is received within the first connector proximal end opening 138. The first connector 130 and second connector 132 are operatively coupled by a threading engagement between the first connector threaded first piece 146 and the second connector threaded second piece 145. Alternatively, the first connector 130 and second connector 132 are operatively coupled mechanically, chemically, and/or chemical-mechanically. In one embodiment for example, the first connector 130 and second connector 132 are crimped, friction fit, press fit, and/or wedged into engagement. In another embodiment for example, the first connector 130 and second connector 132 are operatively coupled by glue, adhesives, resins, welding (laser, spot, etc.), soldering, brazing, adhesives, chemical bonding materials, or combinations thereof.

FIG. 2B shows the second connector threaded second piece 145 operatively coupled to the first connector threaded first piece 146 such that the second connector proximal portion 135 is proximal to the first connector proximal portion 134 and the second connector distal portion 137 is located at or near the first connector distal portion 136. As shown in FIG. 2B, the second connector engaging surface 143 is spaced proximal to the first connector engaging surface 142 for receiving and compressing a strain relief member second end portion therebetween.

Figure 2C:
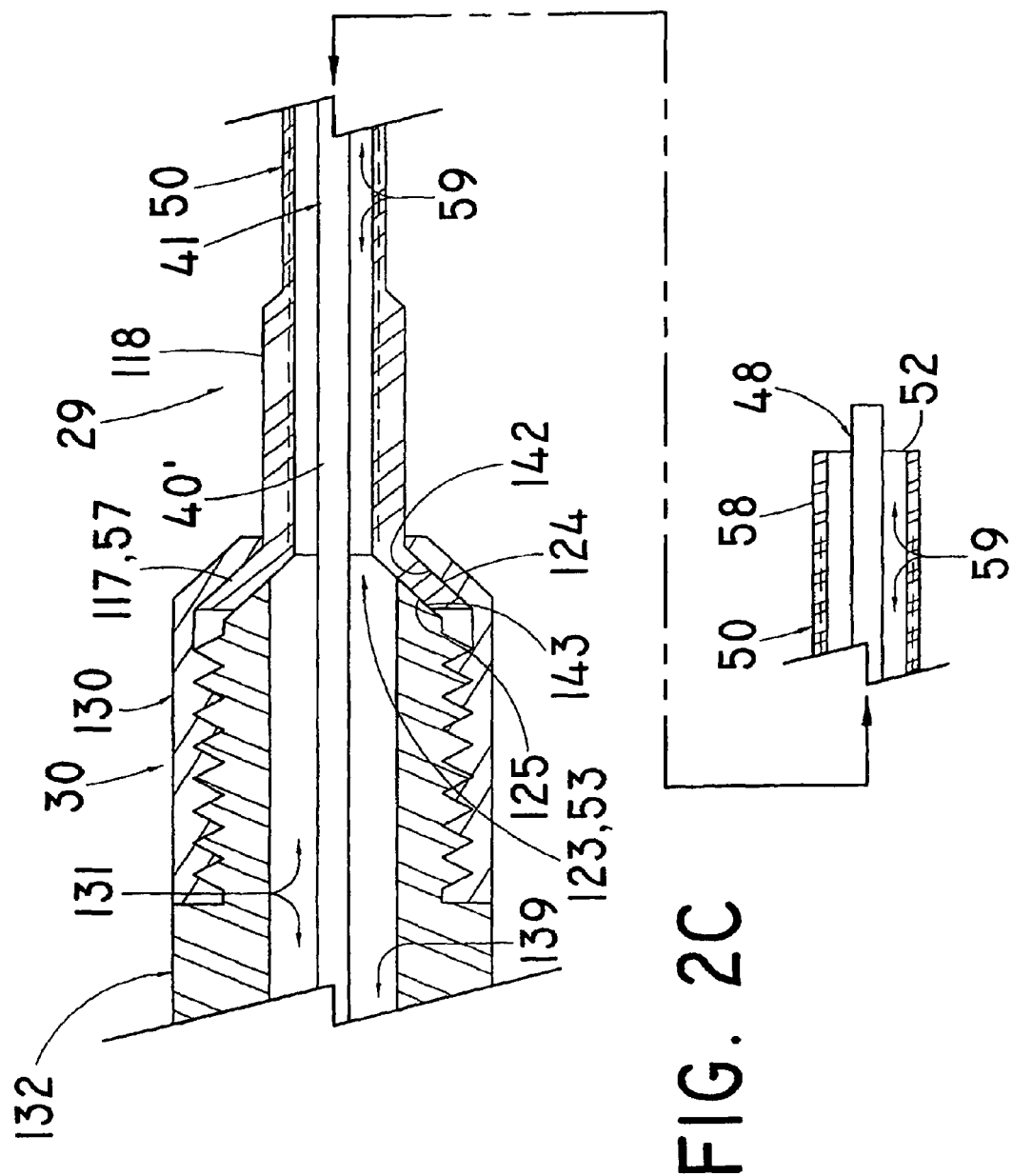
FIG. 2C shows a longitudinally sectioned side view of a handle first connector and a handle second connector according to FIG. 2B operatively coupling a strain relief member and/or an outer sheath according to one embodiment of the invention.

FIG. 2C shows one embodiment of an optional strain relief member 29 comprising a tubular first end portion 118 and a flared second end portion 117. According to FIG. 2C, the medical device delivery system includes an elongate outer sheath 50 (FIGS. 3, 4, 5, 6, 7). Like elements from the previous drawings, embodiments, and description from above are labeled the same. The term elongate is used, not lexicographically but instead, to describe embodiments according to the embodiment that measures at least about 50.0 cm or measures within one of the ranges of lengths exceeding 50.0 cm and as more fully discussed above.

More particularly, FIG. 2C shows that the outer sheath 50 comprises a proximal end portion 57 and a distal end portion 58. The distal end portion 58 comprises an opening 52 and the proximal end portion 57 comprises an opening 53; the openings define a passageway 59 therebetween. In one exemplary embodiment according to FIG. 2C, the strain relief member tubular first and second end portions 118, 117, respectively, are disposed about and operatively coupled to the outer sheath proximal end portion 157. In another embodiment, the tubular first end portion portion 118 disposes about the outer sheath proximal end portion 157 while the flared second end portion portion 117 extends proximally from outer sheath proximal end portion 157. In addition, the strain relief member second end portion portion 117 and/or outer sheath proximal end portion 57 comprise an opening 123 in fluid communication with the outer sheath passageway 59.

By way of example only and not by way of limitation, the terms "operatively coupling," "operatively coupled," "coupling," "coupled," and variants thereof are not used lexicographically but instead are used to describe embodiments of the invention having a point, position, region, section, area, volume, or configuration at which two or more things are mechanically, chemically, and/or chemical-mechanically bonded, joined, adjoined, connected, associated, united, mated, interlocked, conjoined, fastened, held together, clamped, crimped, friction fit, pinched, press fit tight, nested, wedged, and/or otherwise associated by a joint, a junction, a juncture, a seam, a union, a socket, a melt bond, glue, adhesives, resins, welding (laser, spot, etc.), soldering, brazing, adhesives, chemical bonding materials, implanted arrangement, or combinations thereof.

FIG. 2C shows the strain relief member second end portion 117 and/or outer sheath proximal end portion 57 being operatively coupled between the first connector 130 and the second connector 132, and the second connector lumen 131 being in fluid communication with the outer sheath passageway 59. In one embodiment, the strain relief member second end portion portion 117 and/or outer sheath proximal end portion 57 comprises a first opposing surface 124 and a second opposing surface 125. The first connector engaging surface 142 is disposed against the first opposing surface 124 and the second connector engaging surface 143 is disposed against the second opposing surface 125, whereby the strain relief member second end portion 117 and/or outer sheath proximal end portion 57 becomes operatively coupled between the first and second connector engaging surfaces 142, 143, respectively. In one embodiment, the operatively coupled strain relief member second end portion 117 and/or outer sheath proximal end portion 57 is compressed (e.g., sandwiched) between the first and second connector engaging surfaces 142, 143.

Thus, the check flow body 38 provides an optional three way connector. The check flow body proximal mating end 38" and handle coupling member 32 are operatively coupled. The side port is controlled by the detachable connector cap 39. The body distal mating end 38' is operatively coupled to a second connector cap 39', or optionally the handle second connector 132 is received within and operatively coupled to a handle second connector cap 130.

The foregoing description of a proximal portion 12 of a medical device delivery system 10 according to one embodiment of the invention may be one assembly during shipping, or may include a two-part assembly or more. Otherwise stated, the stylet 20 and handle 30 may be sold already combined or may be combined after purchase by inserting the stylet cannula 23 into the handle at the hospital via the threaded tapered plug 21 and threaded tapered receptacle 22. An optional safety lock 34 helps to ensure against unintentional actuation by preventing distal movement of the stylet distal end 20" by extending inwardly within the handle chamber 30 through a slot in the handle outer wall distal to the handle proximal aperture 30'. Consequently, the optional safety lock 34 thereby maintains the handle 30 in an undeployed position until the physician is ready to deploy an implantable prosthesis (e.g., a self-expanding, balloon expandable, or non-expanding stent; prosthetic valve devices, and other implantable articles) at a selected location inside a patient's body.

Middle Section Delivery Device

A delivery system 10 as shown in FIGS. 1 and 2 comprises a middle section delivery device 14. According to the invention, the middle section delivery device 14 is intermediate the proximal portion 12 (FIGS. 1, 2) and the distal portion 13 (FIGS. 1, 2) of the delivery system 10. The term "intermediate" is intended to describe embodiments of the invention whereby the middle section delivery device 14 is intermediary, intervening, lying or occurring between two extremes, or spatially in a middle position, state, or nature—though not necessarily equidistant—between the distal tip of the distal portion 13 and the proximal tip of the proximal portion 12. Furthermore, the middle section delivery device 14 may overlap or be partially inserted into a portion of the distal portion 13 and/or the proximal portion 12. In another embodiment, a portion of the middle section delivery device 14 (such as the sheath 50 explained below) and the distal end portion outer guide channel member 80 (discussed below; see FIGS. 4, 5, 6, 7) may be an elongate tubular catheter or Flexor® sheath of integral construction.

According to the invention, a middle section delivery device 14 is a flexible, elongate (long, at least about 50.0 centimeters ("cm")) tubular assembly. In one embodiment, the middle section delivery device 14 is from approximately 100.0 centimeters ("cm") to approximately 125.0 cm for use when placing a distal portion 13 of the invention within a patient's body, although it may be sized longer or shorter as needed depending on the depth of the target site within the patient's body for delivering the stent. The term "tubular" in describing this embodiment includes any tube-like, cylindrical, elongated, shaft-like, rounded, oblong, or other elongated longitudinal shaft extending between the proximal portion 12 and the distal portion 13 and defining a longitudinal axis. As used herein and throughout to describe embodiments of the invention, the term "longitudinal axis" should be considered to be an approximate lengthwise axis, which may be straight or may at times even be curved because the middle section delivery device 14, for instance, is flexible and the distal portion 13 also may be substantially or partially flexible.

A middle section delivery device 14 comprises an outer sheath 50 (e.g., FIGS. 2, 2C, 5, 6, 7). FIG. 2C shows that the outer sheath 50 is generally tubular and comprises a proximal end portion 57 and a distal end portion 58 and defining a passageway 59 therebetween (e.g., FIG. 2C). In one embodiment, the distal end portion 58 comprises an opening 52 and the proximal end portion 57 comprises an opening 53, which openings define the passageway 59. The middle section delivery device 14 further comprises an elongate inner compression member 41 (e.g., FIGS. 2, 2C, 5, 6, 7). The outer sheath passageway 59 is configured for slideably receiving the inner compression member 41, a catheter, or other medical device.

Figure 3:
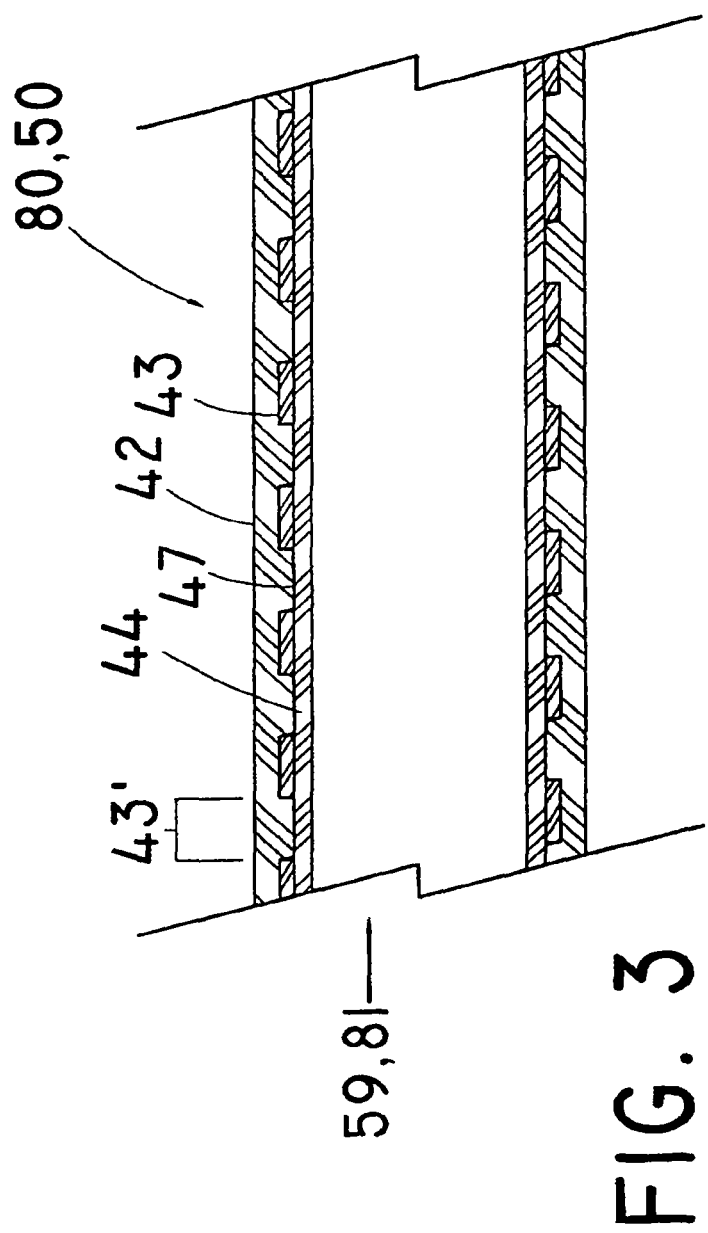
FIG. 3 is a longitudinally sectioned view along a partial length of an embodiment of a catheter used for an outer sheath of a middle section and/or for an outer guide channel member of a distal end of a medical device according to the invention.

FIG. 3 depicts an enlarged, longitudinally sectioned view along a partial length of one embodiment of an outer sheath 50 for use as the middle section delivery device 14, with the delivery system's proximal and distal portions 12, 13, respectively, of the device being removed for clarity. In one embodiment, the outer sheath 50 comprises three layers: an inner layer 44 comprising Teflon material; a middle layer comprising a stainless steel circumferential spiral coil 43; and an outer layer 42 comprising a nylon, a polyether block amide ("PEBA"), and/or other melt bonding material discussed below. The outer layer 42 and inner layer 44 optionally may comprise a lubricious material, one example of which includes a fluorocarbon such as polytetrafluoroethylene (PTFE), to present a slideable surface to allow easier inserting and retracting the middle section delivery device 14 for deploying a self-expanding stent, as will be explained later.

The wall of the inner layer 44 of the outer sheath 50 has sufficient radial rigidity to decrease any tendency of bulging, kinking, and the like under an internal radial expansile force. In other words, the inner layer 44 resists an inner object from protruding or becoming embedded into the inner layer 44, which is beneficial to the slidability of an outer sheath 50. The coil 43 may be compression fitted or wound around the inner layer 44. The coil 43 includes a plurality of turns, and preferably includes uniform spacings 43' between the turns of the coil 43. The coil 43 may be formed of any suitable material that will provide appropriate structural reinforcement, such as stainless steel flat wire or biologically compatible metals, polymers, plastics, alloys (including super-elastic alloys), or composite materials that are either biocompatible or capable of being made biocompatible.

Although the embodiment in FIG. 3 shows a flat ribbon shaped wire coil 43, coils of other cross-sectional dimensions, such as round wire, may also be used. When flat wire stainless steel is used, the coil 43 is optionally formed from wire that is about 0.003 inches thick by about 0.012 inches wide. In one embodiment, the turns of coil 43 are uniformly spaced 43' apart by approximately 0.0118 inches. While FIG. 3 shows an embodiment that uses coils 43 having uniformly spaced turns and a constant pitch, this is not required and coils 43 may be spaced 43' by non-uniform distances or at varying distances. In one embodiment, the ends of coil 43 are positioned approximately 0.197 inches proximal to the distal portion 13 and approximately 0.591 inches distal to the proximal portion 12.

The outer sheath 50 for use with the middle section delivery device 14, and the outer guide channel member 80 (FIGS. 4, 5, 6, 7) and/or the inner guide channel member 70 (FIGS. 4, 5, 6, 7) for use with the distal portion 13, are available for purchase from Cook Incorporated, of Bloomington, Ind. under the trade name of "Flexor®." Examples of the Flexor® sheath devices, materials, and methods of manufacturing them are found in U.S. Pat. Nos. 5,700,253 and 5,380,304, the contents of which are incorporated herein by reference. The Flexor® sheath is particularly suited for the outer sheath 50 of the middle section delivery device 14 and/or the outer guide channel member 80 of the distal second end portion 13 due to its thin PTFE liner on the inside wall of the inner layer 44, thin flat wire coil 43, and Nylon and/or PEBA overcoat 42 that captures the coil 43 and PTFE liner 44 and binds the structure together. The PTFE inner layer 44 of the Flexor® sheath resists an expansile inner object from protruding or becoming embedded into the inner layer 44 and, thereby, provides a slick, smooth surface that slides (e.g., across the surface of a stent if the Flexor® sheath is used with the distal portion 13 or across the surface of an inner compression member 41 if the Flexor® sheath is used with the middle section 14) relatively easily when retracted to expose, release, and deploy the stent or allow the outer sheath 50 to move relative to the inner compression member 41, and the outer guide channel member 80 to move relative to the inner guide channel member 70, during deployment of the stent.

As an alternative to purchasing the outer sheath 50 for use with the middle section 14 and the outer guide channel member 80 for use with the distal portion 13 from Cook Incorporated, one may manufacture the outer sheath and outer guide channel member from various component parts. For instance, one may purchase a tubular inner layer 44 comprising a lubricious material comprising a fluorocarbon such as polytetrafluoroethylene (PTFE or Teflon) from Zeus, Inc. in Orangeburg, S.C., and dispose that inner layer 44 over a mandrel. Alternatively, a sheet of material comprising Teflon may be positioned on a mandrel and formed into a tubular body for the inner layer 44 by any suitable means known to one skilled in the art.

The tubular inner layer 44 (whether formed from a sheet on a mandrel or purchased as a tube and slid onto a mandrel) may be slightly longer than the desired length described above for the outer sheath 50 and/or outer guide channel member 80, and slightly longer than the mandrel. In one embodiment, the tubular inner layer 44 may extend about 5.0 cm from each mandrel end. As explained below, the "loose" ends of the tubular inner layer 44 help during manufacturing of the device.

The mandrel-tubular inner layer 44 assembly is prepared for a middle layer comprising a stainless steel circumferential spiral coil 43 as described above and available for purchase from Cook Incorporated or Sabin Corporation in Bloomington, Ind. As purchased, the coil 43 comes in a long, pre-coiled configuration and will be cut by hand or machine to the desired length either before or after winding the coil about the inner layer 44 to the desired length. As an alternative, one may manufacture the coil from raw material available from Fort Wayne Medical in Fort Wayne, Ind., and process it into a spiral coil 43 shape.

The operator may apply the spiral coil 43 about the mandrel-tubular inner layer 44 assembly by hand or machine. If by hand, then an end of the spiral coil 43 may be started onto the tubular inner layer 44 by any suitable means, for example, such as hooking and winding (e.g., wrapping) the coil 43 around the tubular inner layer 44 in a pigtailed manner at an initial position a desired distance (e.g., 5.0 cm or more) from a first end of the tubular inner layer 44 and to a terminating position that is a desired distance (e.g., 5.0 cm or more) from a second end of the tubular inner layer 44, and then cutting the coil 43 at the terminating position before or after hooking the coil 43 onto the inner layer 44. If by machine, then chucks, for instance, may hold the opposing ends of the mandrel-tubular inner layer 44 assembly while the spiral coil 43 is threaded through an arm on a machine and started onto the tubular inner layer 44 at the initial position as described above. As the chucks rotate, the inner layer 44 rotates, and the arm moves axially down the length of the inner layer 44, thereby applying the coil 43 in a spiral configuration about the inner layer 44. The machine arm moves to a terminating position where the machine or operator cuts the coil before or after hooking the coil 43 onto the inner layer 44.

An operator then applies an outer layer 42 about the coil-inner layer-mandrel assembly. The outer layer 42 may comprise a polyether block amide, nylon, and/or a nylon natural tubing (individually and collectively, "PEBA" and/or "nylon"). The outer layer 42 preferably has a tubular configuration that disposes about (e.g., enveloping, surrounding, wrapping around, covering, overlaying, superposed over, encasing, ensheathing, and the like) a length of the coil-inner layer-mandrel assembly.

Heat shrink tubing, available from many suppliers, including Zeus, Inc. in Orangeburg, S.C. for instance and also Cobalt Polymers in Cloverdale, Calif., may be disposed about the outer layer-coil-inner layer-mandrel assembly. Heating the assembly causes the outer layer 42 to melt. The inner surface of the outer layer 42 thereby seeps through spaces 43' in or between middle layer coils 43 and bonds to both the outer surface of the inner layer 44 and the coils 43. In one embodiment, the inner surface of the outer layer 42 forms a melt bond 47 (explained below) to the outer surface of the inner layer 44. Upon cooling, a solid-state bond results such that the assembly comprises the three layers discussed above. The operator removes the shrink wrap (e.g., by cutting) and withdraws the mandrel. The operator may cut the Flexor® sheath to a desired length for an outer sheath 50 and/or outer guide channel member 80.

The temperature, total rise time, and dwell time for the heat shrink-outer layer-coil-inner layer-mandrel assembly will vary depending on many factors including, for instance, the actual melt bonding material that the outer layer 42 comprises, and also the diameter of the desired Flexor® sheath. For example, the baking parameters for a 2.5 French Flexor® sheath may be approximately 380 degrees Fahrenheit for about five minutes, while the baking parameters for a 4 French Flexor® sheath may be approximately 380 degrees Fahrenheit for about six minutes.

As an alternative to a Flexor® sheath, the outer sheath 50 may comprise a construction of multifilar material. Such multifilar material or tubing may be obtained, for example, from Asahi-Intec USA, Inc. (Newport Beach, Calif.). Materials and methods of manufacturing a suitable multifilar tubing are described in Published United States Patent Application 2004/0116833 (Koto et al.) having an application Ser. No. 10/611,664 and entitled, "Wire-Stranded Hollow Coil Body, A Medical Equipment Made Therefrom and a Method of Making the Same," the contents of which are incorporated herein by reference. Use of multifilar tubing in a vascular catheter device, for instance, is described in U.S. Pat. No. 6,589,227 (Sonderskov Klint, et al.; Assigned to Cook Incorporated of Bloomington, Ind. and William Cook Europe of Bjaeverskov, Denmark), which is also incorporated by reference.

In addition to the outer sheath 50, the middle section delivery device 14 further comprises an inner compression member 41. The delivery device 14 (and, thus, the outer sheath 50 and inner compression member 41) may be constructed to have any diameter and length required to fulfill its intended purposes.

The outer sheath 50, for instance, may be available in a variety of lengths, outer diameters, and inner diameters. In one embodiment, the outer sheath 50 may have a substantially uniform outer diameter in the range from approximately 2 French to approximately 7 French, and in one embodiment the diameter is from approximately 4 French to approximately 5 French in diameter. Otherwise stated, the outer sheath 50 may range from about 0.010 inches to about 0.090 inches in diameter, and in one embodiment the diameter is approximately 0.050 inches. Likewise, the passageway 59 may be available in a variety of diameters. In one embodiment, the inner diameter ranges from about 0.032 inches to about 0.040 inches, and in a preferred embodiment the passageway 59 is approximately 0.032 inches. The diameter may be more or less than these examples, however, depending on the intended vessel passageway for the device. For instance, a larger vessel passageway (e.g., greater expandable inner diameter) may tolerate a bigger device with an outer sheath 50 having a correspondingly greater diameter. Conversely, a narrower vessel passageway may require a thinner outer sheath 50. Likewise, the overall length may vary. In one embodiment, the outer sheath 50 will have a length from about 50.0 cm (or about 19.685 inches) to about 125.0 cm (or about 49.213 inches), and more particularly between about 70.0 cm (or about 27.559 inches) and about 105.0 cm (or about 41.339 inches), and in yet another embodiment the length is approximately 100.0 cm (or about 39.370 inches).

The inner compression member 41 comprises an elongated pusher bar, stiffening member, or stiff polymer that helps to "push" the stent by pushing the stent carrying inner guide channel member at or near the distal portion 13 in order to counter the urge for the stent or stent carrying member to move as a result of an outer sheath or outer guide channel member being pulled over the stent; thereby "pushing" holds the stent in place at the desired deployment site within the patient's body. The inner compression member 41 "pushes" the stent by helping to prevent or minimize the inner guide channel member from prolapsing, recoiling, kinking, buckling, or moving; thereby keeping the inner guide channel member's stent platform on which the stent is disposed (discussed later) substantially stationary, for the most part, relative to the proximal retraction of the distal outer guide channel member (discussed below) that exposes and, thus, deploys the stent. The phrase "at or near" as used herein to describe an embodiment of the invention includes a location that is at, within, or a short distance such as about 0.1 cm to about 15.0 cm, although other ranges may apply, for instance from about 0.5 cm to about 10.0 cm.

The overall length of the inner compression member 41 may vary, as desired. In one embodiment the inner compression member 41 has a length from about 50.0 cm to about 175.0 cm, and more particularly between about 75.0 cm and 150.0 cm, and in one embodiment the length is approximately 125.0 cm to about 140.0 cm. A portion of the inner compression member 41 (e.g., the proximal end 40 and/or middle section 40') may be contained within the handle 30 and the stylet 20, as explained above (FIG. 2).

Likewise, the diameter or width of the inner compression member 41 may vary. In one embodiment, the inner compression member 41 has a diameter or width ranging from about 0.010 inches to about 0.030 inches, by way of example only and not by way of limitation. In one embodiment, the inner compression member 41 has a diameter or width that is approximately 0.016 inches. The diameter or width may be more or less than these illustrative ranges. For example, a deeper target site within a patient may require a thicker inner compression member 41 for greater push-ability, but may tolerate lesser flexibility. In addition, the material that the inner compression member 41 comprises determines whether a smaller and more flexible inner compression member 41 will give suitable flexibility, and also determines whether a wider inner compression member 41 may have the flexibility of a thinner inner compression member 41 made of different material. Furthermore, the inner compression member 41 may have a curved transverse cross-section, such as, for example, a circular cross-section, or it may have a polygonal cross-section, such as, for example, a rectangular cross-section. Alternatively, the transverse cross-section of the inner compression member may include both curved and straight portions. According to one embodiment, the inner compression member 41 may have a nonuniform diameter or width along its length. These various diameters, widths, and cross-sections may occur at the inner compression member proximal end 40, the inner compression member middle section 40', and/or the inner compression member distal mating end portion 48.

It should be understood that the diameter, width, and/or cross-section of the inner compression member 41 may taper. For example, the inner compression member 41 may taper toward the distal end portion as taught in the United States Provisional Patent Application filed on Jan. 23, 2006 entitled, "Tapered Inner Compression Member and Tapered Inner Guide Channel Member for Medical Device Delivery Systems" and having an application Ser. No. 60/761,676, and the non-provisional application filed on Apr. 20, 2006 by the same title and claiming the benefit of the filing date application Ser. No. 60/761,676 under 35 U.S.C. §119(e), the disclosures of which are incorporated in its entirety.

Also, an inner compression member 41 may have an outer surface comprising a lubricious PTFE material and/or an inner surface 44 of the outer sheath 50 may comprise a lubricious PTFE material against the inner compression member 41, in order to allow easy retraction of the outer sheath 50, which is in communication with a distal outer guide channel member to deploy a self-expanding stent, as will be explained later.

Generally, the inner compression member 41 and outer sheath 50 may optionally be approximately the same in length, and the axial length of coil 43 will be less than the length of the inner compression member and outer sheath. In one embodiment, however, the inner compression member 41 comprises a proximal end 40 that extends proximal relative to the outer sheath. In yet another embodiment, the inner compression member extends to a position that is distal the outer sheath. In still another embodiment, the inner compression member 41 stops short of extending all the way to the distal tip of the delivery system 10, and may stop generally from 10 to 40 cm short of the distal tip of the delivery system 10, and in one embodiment it stops approximately 20 to 25 cm short of the distal tip of the delivery system 10, where the distal end portion of the inner compression member 41 is operatively coupled to a proximal portion of an inner guide channel member.

System Distal Portion 13

Now turning to embodiments of a distal portion 13 of medical device delivery systems according to the invention, FIGS. 4, 5, 6, and 7 show the distal portion 13 to be a relatively tubular body. Given the configuration of vessels, vessel passageways, a working channel of an endoscope, or an external accessory channel device used with an endoscope to be navigated, a mostly tubular distal end with a distal tapered, rounded, chamfered, or arrowhead shape may be better tolerated by the patient. Further, in certain embodiments, the distal portion of the distal portion 13 may be soft, rounded, and flexible so as to provide further protection for and care to the patient.

Figure 4:
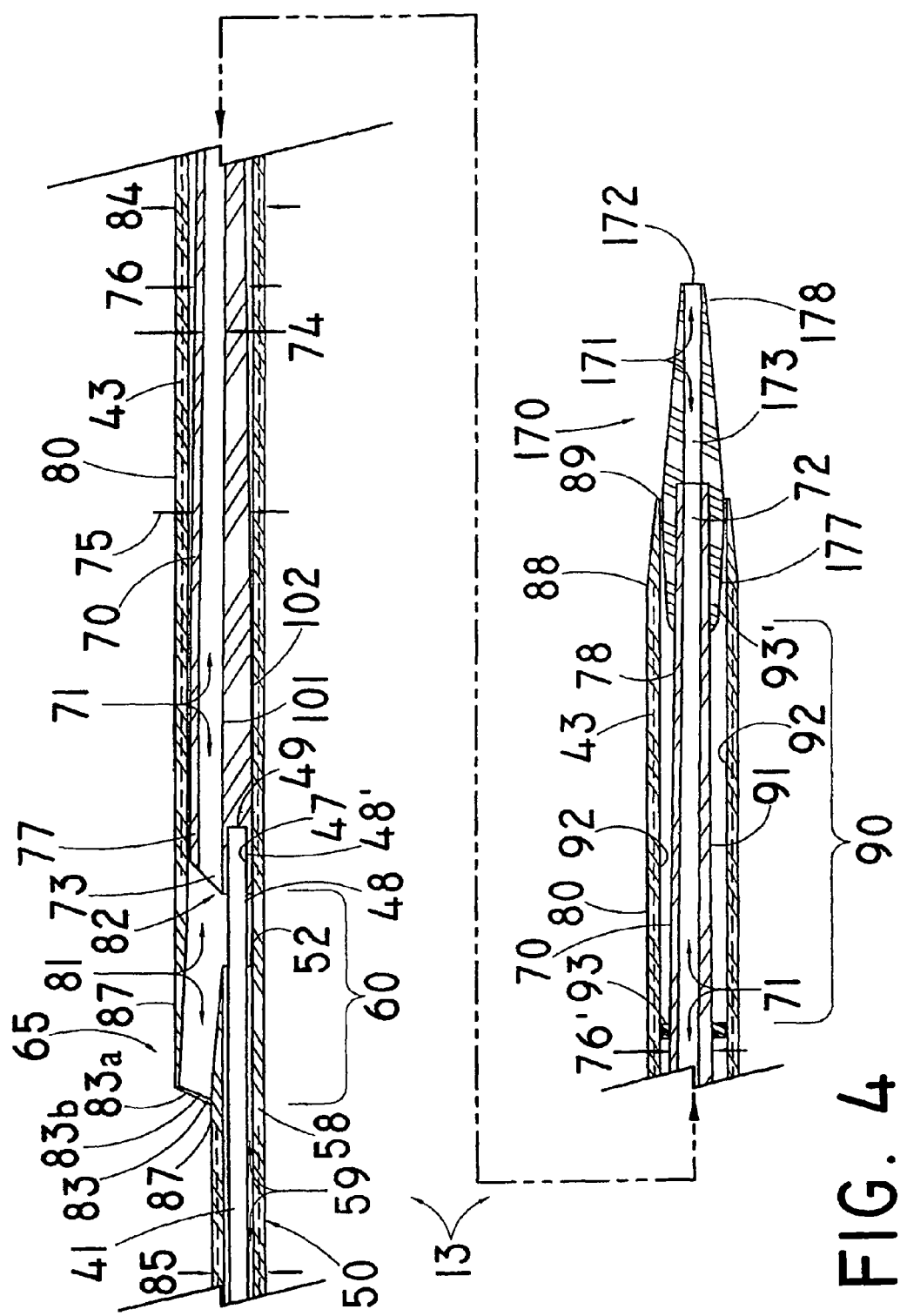
FIG. 4 is a longitudinally sectioned view, broken away, of a distal end of medical device delivery system according to one embodiment of the invention.

FIG. 4 illustrates an embodiment of the distal portion 13 of a delivery system for the rapid insertion of self-expanding stents (for example) comprising an inner guide channel member 70, an outer guide channel member 80 axially slideable relative to the inner member 70, a self-expanding deployment device mounting region 90 (e.g., a stent mounting region), and a transition region 60. As used in connection with describing embodiments of the inner and outer guide channel members 70, 80, respectively, the term "guide channel" is understood to be any aperture, bore, cavity, chamber, channel, duct, flow passage, lumen, opening, orifice, or passageway that facilitates the conveyance, evacuation, flow, movement, passage, regulation, or ventilation of fluids, gases, or a diagnostic, monitoring, scope, catheter, other instrument, or more particularly a wire guide (FIG. 6) or another component of the distal end portion (e.g., an inner member 70 relative to the outer member channel 81).

The distal portion 13, according to the delivery system 10 and shown in FIGS. 4, 5, 6, and 7, may be made of any suitable material (natural, synthetic, plastic, rubber, metal, or combination thereof) that is rigid, strong, and resilient, although it should be understood that the material may also be pliable, elastic, and flexible. By way of illustration only and not by way of limitation, the distal end portion may comprise one or a combination of the following materials: metals and alloys such as nickel-titanium alloy ("nitinol") or medical grade stainless steel, and/or plastic and polymers such as polyether ether-ketone ("PEEK"), polytetrafluoroethylene (PTFE), nylon and/or a polyether block amide ("PEBA"), polyimide, polyurethane, cellulose acetate, cellulose nitrate, silicone, polyethylene terephthalate ("PET"), polyamide, polyester, polyorthoester, polyanhydride, polyether sulfone, polycarbonate, polypropylene, high molecular weight polyethylene, polytetrafluoroethylene, or mixtures or copolymers thereof, polylactic acid, polyglycolic acid or copolymers thereof, polycaprolactone, polyhydroxyalkanoate, polyhydroxy-butyrate valerate, polyhydroxy-butyrate valerate, or another polymer or suitable material. Where it will not contact the patient (e.g., it is contained within a sheath, working channel of an endoscope, or an external accessory channel device used with an endoscope), the middle section delivery device 14 and distal portion 13 do not need to be biocompatible. In contrast, where there is the possibility of patient contact, the material may need to be biocompatible or capable of being made biocompatible, such as by coating, chemical treatment, or the like.

The inner and outer guide channel members 70, 80, respectively, may be made of any suitable material described above for use with the distal portion 13. In one embodiment, the inner guide channel member 70 and the outer guide channel member 80 comprise PEEK material, which has the advantage of softening under heat before burning or degrading. PEEK tubing may be purchased from many suppliers, such as Zeus, Inc. in Orangeburg, S.C. for instance.

Beginning with the inner guide channel member 70, a description will follow relating to features common to embodiments of a distal portion 13 of a delivery system 10 for the rapid insertion of "stents" according to the invention. The inner guide channel member 70 is generally tubular and comprises a first end portion 78 and a second end portion 77 defining a wire guide channel 71 therebetween. Optionally, the inner guide channel member 70 is configured to be slidably nested, fitted, secured, or otherwise positioned within the outer guide channel member 80 such that at least one of the inner guide channel member first or second end portions 78, 77, respectively, is axially intermediate an outer guide channel member first end portion 88 and an outer guide channel member second end portion 87.

The first end portion 78 of the inner guide channel member 70 further comprises a wire guide entry port 72, and the second end portion 77 has a wire guide exit port 73. The entry and exit ports 72, 73, respectively, define and are in communication via the wire guide channel 71. A port, in describing an embodiment of an inner guide channel member 70 and an outer guide channel member 80 according to the invention, includes any structure that functions as an entry or exit aperture, cutout, gap, hole, opening, orifice, passage, passageway, port, or portal. The inner guide channel member entry port 72 is sized to receive a wire guide into the inner member guide channel 71, and the inner guide channel member 70 is configured so that the wire guide may exit proximally out the inner guide channel member exit port 73. Optionally, the exit port 73 is located at or near the transition region 60. In one embodiment of the present invention, the inner member 70 is a cannula (or catheter) having an entry port 72 and an exit port 73 as previously described and defining a guide channel 71 therebetween.

The inner guide channel member 70 further comprises an outer self-expanding deployment device mounting region 90 (e.g., an outer stent mounting region) positioned intermediate the inner guide channel member entry and exit ports 72, 73, respectively. The length of the inner guide channel member 70 of any of the embodiments of the present invention may vary generally from about 10.0 to about 40.0 cm. In one alternative embodiment, the length of the inner guide channel member 70 is approximately 15.0 to approximately 25.0 cm. In another embodiment, the length of the inner guide channel member 70 is approximately 20.0 cm. Also, the length of the inner guide channel member 70 may depend on the intended stent, and in another embodiment the length of the inner guide channel member 70 is approximately 15.0 cm for an 8.0 cm stent.

The inner guide channel member 70 further comprises inner and outer diameters. In one embodiment, both diameters are substantially uniform over the entire length of the inner guide channel member 70. By way of example, an internal diameter 74 might measure approximately 0.0205 inches at or near the inner guide channel member proximal second end portion 77, at or near the inner guide channel member distal first end portion 78, and intermediate the first and second end portions 78, 77, respectively. Likewise, an inner guide channel member 70 might have an outer diameter 75 that measures approximately 0.0430 inches. Thus, the outer diameter 75 might measure approximately 0.0430 inches at or near the inner guide channel member proximal second end portion 77, at or near the inner guide channel member distal first end portion 78, and intermediate the first and second end portions 78, 77.

In an alternative embodiment to an inner guide channel member 70 having a substantially uniform outer diameter 75 along its length from about the second end portion 77 to about the first end portion 78, the inner guide channel member may also comprise a tapered outer diameter 76. In one embodiment, the inner guide channel member tapers distally to a second outer diameter 76' at or near the inner guide channel member first end portion 78 or intermediate the inner guide channel member first and second end portions 78, 77, respectively. The taper 76 has a decreased cross section, diameter, width, height, area, volume, thickness, and/or other configuration, shape, form, profile, structure, external outline, and/or contour relative to the outer diameter 75. In other words, the inner guide channel member second outer diameter 76' is smaller in cross section, diameter, width, height, area, volume, thickness, and/or other configuration, shape, form, profile, structure, external outline, and/or contour than the outer diameter 75.

FIG. 4 further shows an optional atraumatic tip 170 coupled to the inner guide channel member first end portion 78. Extending distally from the inner guide channel member first end portion 78, the atraumatic tip 170 is tapered, rounded, chamfered, or arrowhead shape to be better tolerated by the patient. The atraumatic tip 170 comprises a distal first end portion 178 with a wire guide entry port 172 and a proximal second end portion 177 with a wire guide exit port 173, whereby the entry and exit ports define an atraumatic tip guide channel 171. The ports 172, 173 and channel 171 are sized to slideably receive a wire guide.

Figure 5:
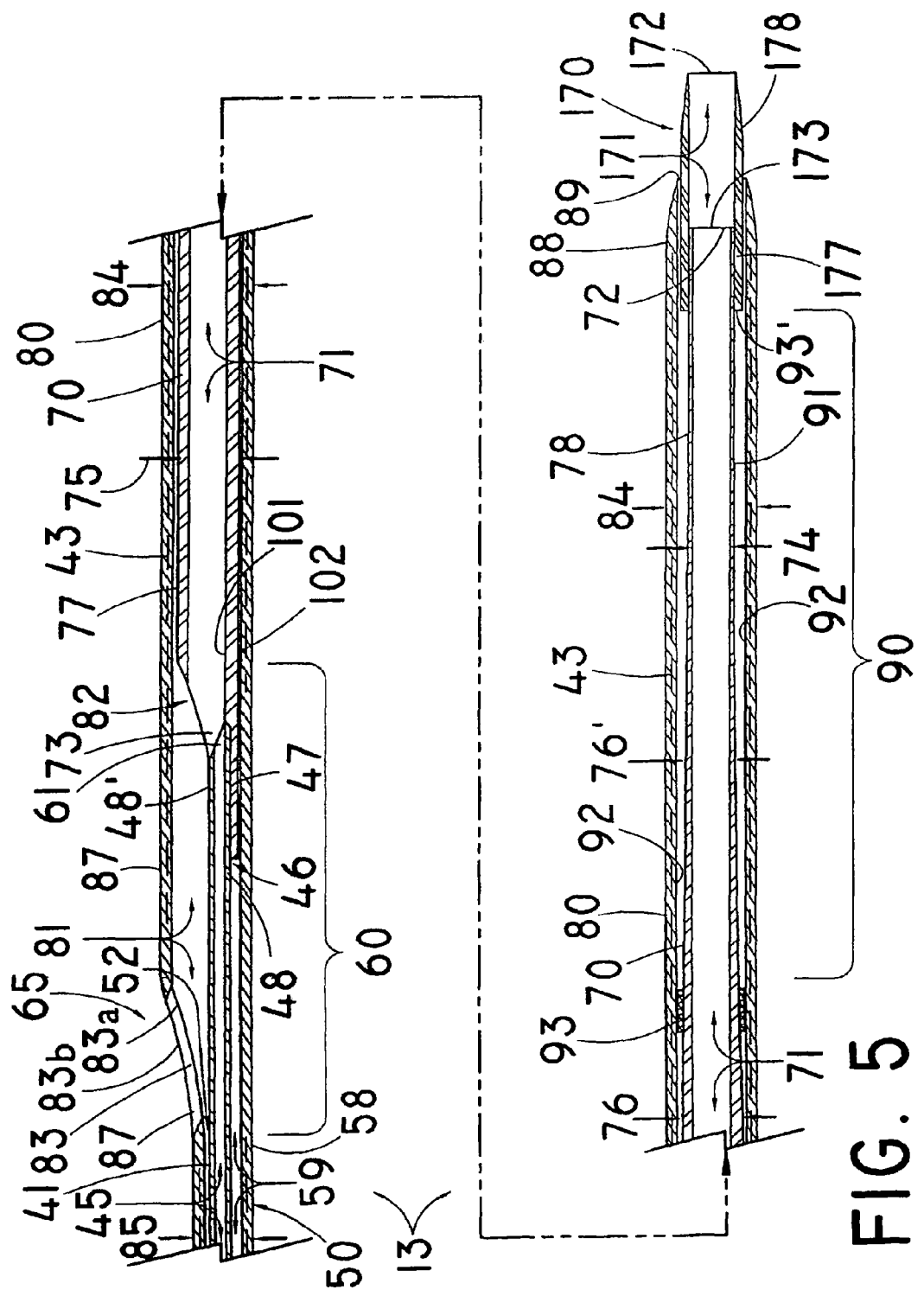
FIG. 5 is a longitudinally sectioned view, broken away, of an alternative embodiment of a distal end of a medical device delivery system according to one embodiment of the invention.

The atraumatic tip second end portion 177, as shown in FIG. 4, may abut the outer guide channel member distal end portion 88 and, thereby, extend entirely distally beyond a distal opening 89 of the outer guide channel member first end portion 88. Optionally, the outer guide channel member distal opening 89 is spaced from the atraumatic tip 170 sufficient to allow delivery system to be flushed with saline that exits the distal portion to remove air in order to help keep air out of the patient, as explained above. In the alternative and as shown in FIG. 5, the atraumatic tip 170 may be configured to have a second end portion 177 that is beveled such that the atraumatic tip second end portion 172 is partially positioned within the outer member guide channel 81 and partially proximal to the outer guide channel member distal opening 89. The beveled design of the atraumatic tip second end portion 177 forms a proximal stop against the outer guide channel member distal opening 89 while permitting the atraumatic tip second end portion 177 to be partially slidably nested, fitted, secured, or otherwise positioned within the outer guide channel member first end portion 88 so that the outer guide channel member first end portion 88 overlaps the atraumatic tip 170 to form a suitable seal that substantially occludes passage of a wire guide between the atraumatic tip 170 and the distal opening 89 of the outer member first end portion 88 (FIG. 5). Furthermore, the atraumatic tip second end portion 177 comprises a stent distal restraint 93' as explained below.

In FIG. 4, the outer guide channel member 80 also is generally tubular and comprises a first end portion 88 and a second end portion 87. The outer guide channel member 80 further comprises a wire guide entry port 82 proximal to the first end portion 88 and a proximal wire guide exit port 83 located at or near the second end portion 87. The entry and exit ports, 82, 83, respectively, define a guide channel 81 of the outer guide channel member 80, wherein the ports 82, 83 and channel 81 are sized to slideably receive a wire guide. The entry port 82 is configured to receive a wire guide into the outer member guide channel 81, and in one embodiment, the entry port 82 is defined by the inner guide channel member exit port 73. In that embodiment, the wire guide moves proximally through the inner member guide channel 71 and egresses from the inner guide channel member exit port 73, wherein the proximal passage of the inner guide channel member exit port 73 is designated as the outer guide channel member wire guide entry port 82. The outer guide channel member proximal wire guide exit port 83 is configured so that a wire guide may egress proximally out the outer member exit port 83. In one embodiment, the outer guide channel member distal opening 89 and exit port 83 define the guide channel 81 therebetween.

In one embodiment, the Flexor® sheath, manufactured and sold by Cook Incorporated of Bloomington, Ind., may be adapted for use with the distal portion 13 and/or the middle section delivery device 14. Otherwise stated, the Flexor® sheath, as shown in FIG. 3 and described above, may be provided for the distal portion 13 and/or the middle section delivery device 14. For instance, the distal portion 13 may be constructed as comprising an integral Flexor® sheath tube with the middle section delivery device 14. Alternatively, a Flexor® tubing may be used for either the middle section delivery device 14 or the distal portion 13, or both. Then, the separable middle section delivery device 14 and distal portion 13 may be attached, adjoined, joined, or combined as taught herein below and/or in the U.S. Provisional Patent Application filed on Apr. 20, 2005 entitled, "Delivery System and Devices for the Rapid Insertion of Self-Expanding Devices" and having an application Ser. No. 60/673,199, and the non-provisional application filed on Apr. 20, 2006 by the same title and claiming the benefit of the filing date application Ser. No. 60/673,199 under 35 U.S.C. §119(e), the disclosures of which are incorporated in its entirety.

The Flexor® sheath has a PTFE inner lining 44 that provides a slick, smooth surface for sliding the outer sheath 50 and/or the outer guide channel member 80 proximally. With regard to the distal portion 13, the outer guide channel member 80 slides relative to the inner guide channel member 70, and the outer guide channel member inner surface 92 would be the inner layer 44 described above, thereby resulting in minimal friction to a stent 17 on the stent platform 91. The slidable inner surface 92 of the Flexor® sheath exhibits a second benefit of minimizing damage or misalignment to the stent. Indeed, because self-expanding stents continuously exert an expanding force against the inside surface 92 of the outer guide channel member 80, any substantial friction or drag between the stent and the inner surface 92 of the outer guide channel member 80 as the outer guide channel member 80 withdraws may damage the stent or cause the stent to be deployed slightly off of the target site.

The thin flat wire reinforcing coil 43 of the Flexor® sheath provides the outer guide channel member 80 with the necessary radial strength to constrain the stent over long periods of storage time. In contrast, where the inner surface 92 of an outer guide channel member 80 does not comprise the Flexor® sheath inner layer 44 or equivalent, the stent over time may tend to become imbedded in the inner surface 92 and, as a result, interfere with retraction of the outer guide channel member 80 at the time of deployment. In an outer guide channel member 80 that comprises a Flexor® sheath, in addition to the inner layer 44 and the reinforcing coil 43, the outer guide channel member 80 has a Flexor® sheath outer layer 42. The outer layer 42 comprises nylon and/or PEBA to provide the necessary stiffness for pushability, retraction, and control of the outer member 80 to facilitate proper deployment of the constrained self-expanding stent. Therefore, the Flexor® sheath is one non-limiting example of an embodiment of an outer sheath 50 and/or an outer guide channel member 80.

While FIG. 4 shows an outer guide channel member 80 having the exit port 83 proximal to the entry port 82 in one embodiment of the outer guide channel member 80, the relative axial distances between the entry and exit ports 82, 83, respectively, vary when the outer guide channel member 80 is in a non-deployed state versus a deployed state, because the outer guide channel member 80 moves axially relative to the inner guide channel member 70. Otherwise stated, FIG. 4 shows an embodiment where the exit port 83 is proximal to the entry port 82 in either a non-deployed stent position or in a deployed stent position. In a non-deployed stent position of another embodiment, however, the exit port 83 may be substantially co-planar to or aligned with the entry port 82. In the fully deployed stent position, the exit port 83 may likewise be proximal, co-planar, or aligned with the entry port 82. Optionally, the entry port 82 and exit port 83 are located at or near the transition region 60 to be discussed below.

Furthermore, the outer guide channel member 80 has a stepped 84, 85 profile, whereby the outer guide channel member 80 comprises a first outer diameter 84 intermediate the outer guide channel member first and second end portions 88, 87, respectively, and a second smaller outer diameter 85 located at or near the outer guide channel member second end portion 87 in the vicinity of the transition region 60 and the breech position opening 65. The stepped 84, 85 profile includes an embodiment where the outer guide channel member 80 transitions to the distal end portion portion 58 of the outer sheath 50 of the middle section delivery device 14. In describing embodiments of the invention, however, the stepped 84, 85 profile shall be discussed in reference to the outer guide channel member 80 in particular, but it should be understood as including a stepped 84, 85 profile in reference to the transition region 60 of the distal portion 13 relative to the middle section delivery device 14 where the middle section delivery device 14 and distal portion 13 are formed from separate units such as, by way of example only and not by way of limitation, separate "Flexor®" sheaths where one comprises a first outer diameter 84 and the other comprises a second smaller outer diameter 85.

As shown in FIG. 4, the second smaller outer diameter 85 of the outer guide channel member 80 is located proximal to the larger first outer diameter 84 and, thereby, comprises a stepped 84, 85 profile. Having a second smaller outer diameter 85 reduces the profile of the outer guide channel member 80 and/or the outer guide channel member 80 transition to the middle section delivery device 14, which is advantageous in procedures involving narrow vessel passageways, endoscope working channels, or accessory channels for use with endoscopes. The difference in the first diameter 84 and the second diameter 85 may vary. By way of illustration, the second diameter 85 may be approximately one-fourth to approximately nine-tenths that of the first diameter 84. In another embodiment, the second diameter 85 may be about one-half that of the first diameter 84. In another embodiment, the first diameter 84 is roughly 5 French while the second diameter 85 is roughly 4 French.

In one embodiment of the stepped 84, 85 profile of the outer guide channel member 80, the second smaller outer diameter 85 is located at or near the outer guide channel member second end portion 87. The second end portion 87 may decrease precipitously from the first outer diameter 84 to the second smaller diameter 85. In a precipitous step, the change from the diameters occurs over a short length along the longitudinal axis of the distal portion 13. In a further example of a precipitous step, the plane formed by the exit port 83 may be substantially perpendicular to the longitudinal axis of the outer guide channel member 80. In an alternative embodiment, the second end portion 87 may decrease gradually from the first outer diameter 84 to the second smaller diameter 85. In a gradual step, the change from the two diameters occurs over a length of more than 1.0 millimeter ("mm") along the longitudinal axis of the distal portion 13 at or near the transition region 60 and breech position opening 65, and in one instance this change occurs over a length from about 1.0 mm to about 10.0 mm. In a further example of a gradual step, the plane formed by the exit port 83 may be at an angle other than 90 degrees relative to the longitudinal axis of the distal portion 13.

FIG. 4 also shows a breech position opening 65 located at or near the second end portion 87 of the outer guide channel member 80 comprising the wire guide exit port 83. In other words, rather than the exit port 83 being an aperture in a lateral sidewall of the outer guide channel member 80 intermediate the first and second end portions 88, 87, respectively, in a breech position opening 65 embodiment the exit port 83 is at the rear, back, or proximal part of the distal portion 13 at or near the outer member second end portion 87 and the stepped 84, 85 profile such that it opens in the direction of the outer surface of the outer sheath 50.

The breech position opening 65 may be used for front-loading and the more common procedure of back-loading a wire guide (or catheter, for instance). In a back-loading procedure for a delivery system having a breech position opening 65, the wire guide may pass proximally through the guide channel 71 of the inner guide channel member 70, proximally through the guide channel 81 of the outer guide channel member 80, and leave the exit port 83 of the second end portion 87 of the outer guide channel member 80 from a breech position opening 65 in a rear, back, or proximal part of the distal portion 13. Conversely, in a front-loading procedure for a delivery system having a breech position opening 65, the physician may feed the wire guide distally into a breech position opening 65 at the rear, back, or proximal part of the distal portion 13 by entering the exit port 83 of the second end portion 87 and the guide channel 81 of the outer guide channel member 80 and through the guide channel 71 of the inner guide channel member 70, where the wire guide may exit from the wire guide entry port 72 of the inner guide channel member 70 and/or wire guide entry port 172 of the atraumatic tip 170.

In a distal portion 13 having a breech position opening 65 that comprises an exit port 83 located at a breech position of the transition region 60 according to the invention, the wire guide does not need to make any sharp turns away from the longitudinal axis of the distal portion 13 that may result in kinking of the wire guide. The breech position opening 65—comprising an exit port 83 according to embodiments of the invention, as those shown in FIGS. 4, 5, 6, and 7 by way of example and not by way of limitation—is located proximal to the inner guide channel member second end portion 77 and may be transverse or angled relative to the tubular distal portion 13 longitudinal axis. In other words, the wire guide exit port 83 may be positioned at or near a breech position opening 65 of the distal portion 13, wherein the exit port 83 is located at or near the rear, back, or proximal part of the outer guide channel member 80 and/or second end portion 87, rather than being positioned exclusively on the side (e.g., outer circumferential cylinder wall) of the outer guide channel member 80.

In FIG. 4, the breech position opening 65 comprises an exit port 83 that is illustrated as being oblique, although other configurations of the exit port may be utilized to aid the wire guide in exiting the rear of the outer member. In one example, the exit port 83 may form a plane substantially perpendicular to the longitudinal axis of the outer guide channel member second end portion 87. In another example, the plane formed by the exit port 83 may be at an angle other than 90 degrees relative to the longitudinal axis of the distal portion 13. Optionally, the oblique exit port 83 of a breech position opening 65 has lateral walls 83a, 83b that act as guide rails to direct a wire guide proximally toward the middle section delivery device 14 and to run along the outside of the outer sheath 50.

The overall axial length of the exit port 83 of the breech position opening 65 may vary. In one embodiment, the length is approximately from about 1.0 mm to about 10.0 mm. Another embodiment has a length of approximately 5.0 mm. The overall width of the exit port 83 may also vary. In one example, the width of the exit port is approximately 1 French. In yet another instance, the width of the exit port 83 ranges from about 1 French to about 4 French. In another example, the width of the exit port 83 may be the approximate difference between the first outer diameter 84 and the second outer diameter 85 of the outer guide channel member 80.

At the transition region 60, the exit port 73 of the inner guide channel member 70 is in communication with the outer guide channel member 80 wire guide entry port 82, while the second end portion 77 is operatively coupled to the distal mating end portion 48 of the inner guide channel member 70 as explained below. The length of the transition region 60 may vary. For instance, the transition region 60 may be approximately from about 0.5 cm to about 10.0 cm. In another embodiment, the transition region 60 has the approximate length of about 5.0 cm. Furthermore, the length of the transition region 60 is variable: from a shorter axial length when the outer guide channel member 80 is in a non-deployed axial position; to a greater axial length when the outer guide channel member 80 retracts proximally to deploy the stent. Likewise, the overall length of the transition region 60 varies in the embodiment where the exit port 83 is distal to the entry port 82 when the outer guide channel member 80 is in a non-deployed stent position, compared to the initial length of the transition region 60 in an embodiment where the exit port 83 is proximal to the entry port 82 when the outer guide channel member 80 is in a non-deployed stent position.

In one use of the transition region 60 according to an embodiment of the invention, the outer guide channel member entry port 82 receives a wire guide from the inner guide channel member exit port 73 and the wire guide thereby is received in the outer member guide channel 81. At the transition region 60, the inner member guide channel 71 and outer member guide channel 81 are approximately aligned relatively coaxially in one embodiment. Approximate alignment of the guide channels 71, 81 facilitates a smooth transition of the wire guide. Smooth transition optimally reduces any bending of the wire guide as the wire guide moves proximally from the inner member guide channel 71 to the outer member guide channel 81.

As shown in FIG. 4, the distal portion 13 also comprises a self-expanding deployment device mounting region 90. This mounting region 90 may be used for implantable prosthesis such as expandable (self-expanding, balloon expandable, or otherwise expanding) and nonexpanding stents, prosthetic valve devices, and other implantable articles for placement inside a patient's body (the implantable prostheses being referred to individually and collectively as "stents" without limiting the invention) and therefore may be referred to as a stent mounting region to include the foregoing implantable prostheses.

The stent mounting region 90 comprises a stent platform 91 on an outside surface of the inner guide channel member 70 located at or near the inner guide channel member second end portion 78. In describing embodiments of the invention, the platform 91 "at or near" the inner guide channel member second end portion 78 includes a region intermediate the inner guide channel member entry port 72 and the inner guide channel member exit port 73. The platform 91 may be any stent mounting surface, including but not limited to the outside surface of the inner guide channel member 70, a recess, or an indentation located at or near the first end portion 78 of the inner guide channel member 70. In a non-deployed state, a self-expanding stent for example (not shown) compresses against the stent platform 91 and disposes around the outside of the inner guide channel member 70.

The stent mounting region 90 controls the lateral movement (e.g., transverse expansion away from the inner guide channel member longitudinal axis) to avoid premature deployment of the stent. In order to control the lateral movement of the stent, the stent is sandwiched between the platform 91 on the inner surface of the stent and the inner surface 92 of the outer guide channel member 80 to keep the stent in a compressed state. Because the stent is bound from above by the inner surface 92 of the outer guide channel member 80 and bound from below by the platform 91 of the inner guide channel member 70, the stent mounting region 90 maintains the stent in a substantially compressed state and controls premature deployment of the stent.

In addition to controlling a stent's lateral movement, the stent mounting region 90 restrains the axial movement of a stent to control the stent movement away from the target site. A proximal restraint 93 controls proximal axial movement of the stent. In one embodiment, the proximal restraint 93 is sized to be large enough to make sufficient contact with the loaded proximal end portion of the stent without making frictional contact with the inner surface 92 of the outer guide channel member 80. In addition to helping to stop the stent's proximal movement in the non-deployed state, this restraint 93 assists with "pushing" the stent out of the distal portion 13 by helping to prevent the inner guide channel member 70 and/or the stent disposed on the stent mounting region 90 from migrating proximally when the outer guide channel member 80 retracts proximally relative to the stationary inner guide channel member 70 in order to expose and deploy the stent. Optionally, the restraint 93 may be radiopaque so as to aid in stent positioning within the vessel passageway at or near the target site within a patient. In one embodiment, an optional distal restraint 93' is large enough to make sufficient contact with the loaded distal end portion of the stent to control axially distal movement of the stent. Similarly, in another embodiment the proximal second end portion 177 of an optional atraumatic tip 170 controls the stent's distal axial movement. Indeed, because the medical device delivery system may be used for deploying an implantable prosthesis that comprises balloon expandable or non-expanding stents, prosthetic valve devices, and other implantable articles at a selected location inside a patient's body, the proximal restraint 93 and distal restraint 93' control the axial distal movement of the implantable prosthesis. Optionally, the distal restraint 93' and/or atraumatic tip 170 may comprise radiopaque materials so as to aid in stent positioning within the vessel passageway at or near the target site within a patient.

FIG. 4 also illustrates that the inner compression member 41 and inner guide channel member second end portion 77 may be operatively coupled by any suitable means. In one embodiment, a melt bond 47 (described below) operatively couples an inner compression member distal mating end portion 48 ("mating end 48" or "mating end portion 48") and the second end portion 77 of the inner guide channel member 70. A melt bond 47 provides surface-to-surface contact between an outer engaging surface 48' of the mating end portion 48 and the inner guide channel second end portion 77, thereby forming a more solid connection between the inner compression member 41 and the inner guide channel member 70.

FIG. 5 illustrates a schematic view showing an alternative embodiment of a distal portion 13 of a delivery system for the rapid insertion of stents comprising an inner guide channel member 70, an outer guide channel member 80 axially slideable relative to the inner member 70, a deployment device mounting region 90 (e.g., a stent mounting region), and a transition region 60. Like elements from the previous drawings, embodiments, and description from above are labeled the same. In this embodiment, the inner compression member 41 optionally comprises a passageway 45 (e.g., hollow, having a lumen) that facilitates the conveyance, ventilation, flow, movement, blockage, evacuation, or regulation of medication and/or fluids or accommodates the insertion of a diagnostic, monitoring, scope, or other instrument.

The tubular inner compression member 41 may have a uniform inside diameter ranging from about 0.0527 to about 0.132 inches. The wall thickness of the tubular inner compression member 41 is approximately 0.0015 inch. These dimensions are illustrative only, and the inner diameter and wall thickness may be constructed to be of any size necessary to accomplish the purposes for which the delivery system is to be employed (i.e., limited by the vessel passageway or working channel in which the device is to be used).

In addition, this inner compression member 41 has an optional distal one-way valve 61. Thus, the valve 61 may serve a dual function. First, a one-way valve is relatively resistant to contamination from bodily fluids entering the inner compression member passageway 45. Second, it allows the movement of medication and/or fluids to exit distally the inner compression member 41 passageway 45 at or near the transition region 60 and may direct medication and/or fluids into the inner member guide channel 71 and/or the outer member guide channel 81.

Indeed, the inner compression member passageway 45 may facilitate using the medical device delivery system for deploying an implantable prosthesis that comprise balloon expandable stents, prosthetic valve devices, and other implantable articles (individually and collectively, "stent") at a selected location inside a patient's body. The stent is disposed at the deployment device mounting region 90 intermediate the proximal restraint 93 and distal restraint 93' to control the axial distal movement of the implantable prosthesis.

In one embodiment for using the delivery system with a balloon expandable implantable prosthesis, the inner compression member distal mating end portion engaging surface 48' operatively couples to the inner guide channel member outer surface 102 (or is welded to an outer surface of a metal cannula that has the inner guide channel member second end portion 77 glued within the cannula lumen), and an inflation member (e.g., a balloon) extends distally from the inner compression member distal mating end portion and is disposed over the proximal restraint 93 and distally about the platform 91 of the stent mounting region 90 such that the balloon is located under the stent. The stent is positioned within the vessel passageway at or near the target site within a patient, wherein the outer sheath 50 and outer guide channel member 80 is axially slideable relative to the inner compression member 41 and inner guide channel member 70 upon corresponding axial slideable movement of the handle 30, thereby exposing and, ultimately, deploying the stent from the stent mounting region 90. The stylet 20 may be adapted to receive a syringe for allowing inflation fluid, such as saline, to travel from and through the proximal end 40 of the inner compression member 41 and out the valve 61 at the distal end portion 48 in order to fill the inflation chamber of the balloon. Therefore, balloon expands under the stent and, as a result, the stent expands radially to plastically deform the stent into a substantially permanent expanded condition. The physician then deflates the balloon and removes the inner guide channel member 70 and remainder of the delivery system from the patient's body. This description of using the delivery system for balloon expandable implantable prosthesis is given by way of example and not by way of limitation. Alternatively, a tubular inflation fluid carrying device is in the outer sheath passageway 59 and extends from the system proximal portion 12 to the system distal portion 13 and operatively couples to an inflation member disposed under the stent.

In one embodiment of the distal portion 13 of a delivery system illustrated in FIG. 5, an internal joint 46 comprises a melt bond 47 that operatively couples the inner guide channel member distal mating end portion 48 and the second end portion 77 of the inner guide channel member 70. For example, the inner compression member outer engaging surface 48' may form a melt bond 47 to the inner surface 101 (or alternatively to the outer surface 102) of the inner guide channel member second end portion 77, as taught above.

The embodiment shown in FIG. 5 also illustrates that the exit ports 83 and 73 may have various configurations. First, these exit ports curve, and second, compared to FIG. 4 they slope over a longer overall axial length to aid the wire guide in exiting the inner member and outer member, respectively. Furthermore, the exit port 83 thereby has longer axial lateral walls 83a, 83b for acting as guide rails to direct a wire guide proximally toward the middle section 14 and to run along the outside of the outer sheath 50.

Moving to the atraumatic tip 170 as illustrated in FIG. 5, this is a little less arrowhead-shaped compared to the atraumatic tip 170 shown in FIG. 4. Instead, the atraumatic tip in FIG. 5 has a second end portion 177 that comprises a right cylindrical tubular configuration. Furthermore, the sides of the atraumatic tip second end portion 177 are more uniformly parallel and do not form a proximal stop against the outer guide channel member distal opening 89 as in a beveled embodiment of the atraumatic tip second end portion 177 as illustrated in FIG. 4. The atraumatic tip second end portion 177 optionally comprises a stent distal restraint 93' for controlling distal axial movement of the implantable prosthesis when the medical device delivery system is used for deploying balloon expandable or non-expanding stents, prosthetic valve devices, and other implantable articles at a selected location inside a patient's body.

Turning now to FIG. 6, that figure shows a partially sectioned distal portion 13 in accordance with an embodiment of the device according to FIG. 5 with a wire guide 16 inserted therein. In a back-loading procedure, the wire guide 16 enters the guide channel 171 of the atraumatic tip 170 and travels proximally toward the inner guide channel member 70. The wire guide 16 then enters the inner member guide channel 71 and travels proximally toward the outer guide channel member 80 via the entry port 82 and enters the outer member guide channel 81 and out the exit port 83. The less common front-loading procedure could be described as above but conversely stated.

In FIG. 6, the inner and outer guide channels 71, 81, respectively, are substantially aligned coaxially along an approximate center longitudinal axis of the distal portion 13. Because the channels 71, 81 are substantially aligned, the wire guide 16 moves through the inner member guide channel 71 to the outer member guide channel 81 and out the outer guide channel member exit port 83 at or near the breech position opening 65 with relatively little kinking, bending, buckling, or bowing. It should be noted that for the ease of showing the wire guide 16, the wire guide 16 proximal to the exit port 83 is shown slightly offset from outer sheath 50, though the wire guide 16 may actually run along the outside of the outer sheath 50 or in a groove (not shown) in the outer sheath 50.

FIG. 7 illustrates a longitudinally sectioned side view showing an alternative embodiment of a distal portion 13 of a delivery system for the rapid insertion of stents comprising an inner guide channel member 70, an outer guide channel member 80 axially slideable relative to the inner member 70, a deployment device mounting region 90 (e.g., a stent mounting region), and a transition region 60. Like elements from the previous drawings, embodiments, and description from above are labeled the same. This embodiment represents an alternative embodiment of a joint 46 for operatively coupling the inner compression member 41 and inner guide channel member 70 with a cannula 95.

In one embodiment, the cannula 95 is a hollow, rigid tube, cylinder, ring, cannula (with or without a trocar), or other coupling device comprising metal such as medical grade stainless steel or super-elastic alloys (e.g., nitinol) to name but a few non-limiting examples. In one embodiment, the cannula 95 comprises a generally right cylindrical configuration or is elliptical, hyperbolic, parabolic, curved, polygonal, rectangular, or irregular in shape or cross section. The cannula 95 is sized for receiving the inner guide channel second end portion 77 and/or the inner guide channel second end portion outer diameter 75. The outer surface 102 of the inner guide channel second end portion 77 is operatively coupled to an inner engaging surface of the securing body 95 by glue, adhesives, resins, chemical bonding materials or combinations thereof and the like (collectively and individually, "glue"). By way of example only, the glue may be Loctite 4061 instant adhesive, formulated to polymerise rapidly in thin films between two surfaces to form rigid thermoplastics. Loctite 4061 instant adhesive is a medical device adhesive particularly suitable for a wide variety of substrates such as rubber, plastics, and metals, ant it is available from the Loctite Corporation.

In addition to securing the outer surface 102 of the inner guide channel member second end portion 77 to an inner engaging surface of the cannula 95, the cannula 95 also operatively couples the inner guide channel member distal mating end portion 48. An outer engaging surface 48' of the mating end portion 48 is in an abutting relationship (e.g., touching, in contact directly or by intervening parts, or adjacent) to an outer engaging surface of the cannula 95, and the mating end portion 48 and cannula 95 are operatively coupled by any suitable means, including but not limiting to welding, soldering, brazing, or fusing. Soldering and brazing are used if a semi-permanent connection between the distal mating end portion 48 and the cannula 95 is desired, because solder or braze metals have a lower melting point than the metals that are joined. Thus, when sufficient heat is applied to melt the solder or braze metal, they form an alloy with the surfaces of the mating end portion 48 and the cannula 95 and, upon solidification, thus form a joint that can be unfastened during manufacturing (e.g., to redo in the event of a poor connection) by reheating without destroying the parts that have been joined. In contrast, welding involves melting the outer engaging surface 48' of the mating end portion 48 and an outer engaging surface of the cannula 95 at the interface, or involves combining temperature and pressure so as to cause localized coalescence. Consequently, in most instances higher temperatures are involved than for soldering, and the union is permanent.

Where the inner compression member distal mating end portion 48 and the cannula 95 are connected, an optional tube may be disposed about the joint 46. The tubing has the advantage of minimizing some of the sharp edges created by a welded, soldered, or fused joint. In one embodiment, the tube is a melt bonding tube disposed about and melt bonded to the joint 46. Whereas FIG. 7 shows the distal most tip of the distal mating end portion 48 flush with (e.g., substantially co-planar) the distal end portion of the cannula 95, it may alternatively be set back approximately 0.5 mm proximally from the distal end portion of the cannula 95. The set back arrangement allows solder, weld, or fusion to form a smooth transition and fill the space between that distal end tip and the cannula 95. This would also minimize the profile compared to placing more of a circumferential solder, weld, or fusion about the joint.

According to FIGS. 7, 7A, 7B, and 7C, the distal mating end portion 48 comprises a contoured configuration 48" that is complementary to an outer engaging surface 95' of the cannula 95. Thus, in an embodiment comprising a cannula 95 that is curved or otherwise circular in cross-section, then FIG. 7A shows that the contoured configuration 48" is fluted so that the outer engaging surface 48' is capable of being in an abutting relationship (e.g., touching, in contact directly or by intervening parts, or adjacent) relative to a curved or circular outer engaging surface 95' of the cannula 95. A fluted contoured configuration 48" comprises any curved, shoehorn shape, celery shape, semicircular shape, crescent shape, wishbone shape, saddle shape, C-shaped, V-shaped, U-shaped, or other arcuate configuration. In another embodiment, an outer engaging surface 95' of the cannula 95 could have a flat portion, and FIG. 7B shows that the contoured configuration 48" is likewise flat so that the outer engaging surface 48' is capable of being in an abutting relationship (e.g., touching, in contact directly or by intervening parts, or adjacent) relative to the flat portion of the outer engaging surface of the cannula 95. Even when the outer engaging surface 95' of the cannula 95 is curved or circular in cross section, however, FIG. 7C shows that the inner compression member contoured configuration 48" could be flat, because the soldering, brazing, or fusing may fill in the space between the outer engaging surface 48' and a tangent that the flat configuration 48" forms to the curved portion of the outer surface 95' of the cannula 95. Similarly, if welding 96 is used, then the flat configuration 48" will form to a curved or circular outer engaging surface 95' of the cannula 95.

In addition, the contoured configuration 48" maintains low profile, high-strength, and flexibility of the connection between the inner compression member distal mating end portion 48 and the cannula 95. The contoured configuration 48" is in contrast to a rounded inner compression member distal mating end portion 48, which would have a greater diameter at the connection between the inner compression member distal mating end portion 48 and the cannula 95.

In order to create the contoured configuration 48", the inner compression member distal mating end portion 48 may be formed, sheared, casted, or molded. By way of example only, forming can be done both hot and cold (except for stamping, which is always done cold) in order to modify the shape and/or physical properties of the material comprising the inner compression member distal mating end portion 48. Common forming processes include rolling the distal mating end portion 48 (between one or two rollers), stretching, forging, straight bending, and stamping.

Additional embodiments of the joint 46, cannula 95, and inner compression member distal mating end portion 48 comprising a contoured configuration 48" are described in the U.S. patent application filed on Apr. 20, 2006 entitled, "Joint for Operatively Coupling a Contoured Inner Compression Member and an Inner Guide Channel Member for Medical Device Delivery Systems" and having a client reference number PA-5930-RFB, the disclosure of which is incorporated in its entirety.

Melt-Bonded Joint for Joining the Outer Sheath and the Outer Guide Channel Member As used to describe an embodiment of the invention, melt bonding 47 (for shorthand purposes in describing embodiments according to the invention, melt bonding 47 includes implanting 49) comprises any suitable means for melting, liquefying, softening, making semi-molten, molten, fusing, or making malleable, pliant, supple, moldable, ductile, or otherwise penetrable by another component or fused to melt bonding material comprising the other element. For instance, melt bonding 47 involves bringing two components together at an interface, wherein one (or preferably both) of the component interfaces are in at least a semi-melted, molten, softened, sticky, state. In another embodiment, melt bonding 47 comprises both components being melted at the interface and that they may be sufficiently chemically and physically compatible such that they fuse together structurally upon cooling. In yet another embodiment, melt bonding 47 comprises any suitable means for liquefying, melting, or fusing the outer sleeve body 144 to the outer sheath 50 (or first sheath 106) and/or the outer guide channel member 80 (or second sheath 107).

Melt bonding 47 typically requires that one or both of the components have surfaces comprising the same or similar melt-bonding materials or otherwise be sufficiently chemically and physically compatible at the melt-bonding interface such that they fuse together upon cooling. The chemical compatibility may be expressed in terms of having similar values for surface energy and/or solubility parameter. In simple terms, similar materials may tend to have a mutual affinity and a greater propensity to adhere to one another than do dissimilar materials. As used herein, melt bonding 47 includes bonding whereby one component is melted while the other component is at or above its melting point.

In the alternative, the melt bonding materials may be different, so long as they have substantially similar melting points at standard atmospheric pressure such that the materials soften, become semi-molten, molten, or liquefy under heat and thereby fuse together structurally in a solid state melt bond 47 joining the first and second melt bonding materials of the components. If the materials had melting points that were too different at standard atmospheric pressure, then one material may degrade or burn and the like before the second material begins to melt.

Melt bonding 47 may be single layer interface whereby one component interface/surface mates to a second component interface/surface, or may be multi-layer interface whereby one component is implanted 49 into a second component and then surrounded by the second component. The chemical compatibility can best be expressed in terms of having similar values for surface energy and/or solubility parameter. In simple terms, similar materials tend to have a mutual affinity and a greater propensity to adhere to one another than do dissimilar materials. Melt bonding includes bonding whereby one component is melted while the other component is at or above its melting point.

Melt bonding 47 offers advantages to other connecting means for joining two components. For instance, melt bonding 47 requires much less design engineering and overcomes objections presented by fluid adhesive bonding processes. Also, a joint assembly 140 melt bonding 47 an outer sleeve body 144 to an outer sheath 50 (or a first sheath 106) and/or an outer sleeve body 144 to an outer guide channel member 80 (or a second sheath 107), is almost instantaneous once the melting temperature is reached. Furthermore, a joint assembly 140 comprising a melt bond 47 provides surface-to-surface contact between the outer sleeve body 144 and the outer sheath 50 (or first sheath 106) and/or the outer sleeve body 144 and the outer guide channel member 80 (or second sheath 107). Additionally, a solid-state bond forms (e.g., fusing, chemical bonding, and/or cross-linking bonds formed at the melt bonded material interfaces) between the an outer sleeve body 144 and the outer sheath 50 (or first sheath 106) and/or an outer sleeve body 144 and the outer guide channel member 80 (or second sheath 107). As a result, in one embodiment, the outer sleeve body proximal engaging portion and the outer sheath distal end portion (or the first sheath distal end portion) are melt bonded together, and the outer sleeve body distal engaging portion and the outer guide channel member proximal end portion (or the second sheath second end portion) are melt bonded together.

Melt bonding materials may have different "melt bonding" temperatures at which they soften and become almost tacky without substantial degradation. Melt bonding materials are available from vendors, including Zeus, Inc. in Orangeburg, S.C. for instance; Cobalt Polymers in Cloverdale, Calif.; and under the trade name of Pebax® PEBA from the Arkema Group. The melt bonding materials may include one or a combination of a class of suitable materials comprising nylon, nylon natural tubing, polyether block amide (PEBA), polyetheretherketone (PEEK), polytetrafluorethylen (PTFE), polyvinylidene fluoride (PVDF); thermoplastic, acrylonitrile-butadiene-styrene copolymer, ionomers, polyamides, polyesters, polyethylenes, polypropylene, polyamide, ionomer, polycarbonate, polyphenylene oxide (PPO), polyphenylene sulphide (PPS), acrylic, liquid crystal polymer (LCP), polyolefin, polyethylene acrylate acid (PEAA), vinyl; polyvinyl chloride (PVC), polyvinylidene fluoride, polyvinyl, and polyvinyl chloride (individually and collectively, "nylon" and/or "PEBA").

In one embodiment, PEEK material is used for the melt bonding material. PEEK melts at about 633° F., so the material may be heated from about 628° F. to about 638° F. For instance, a radiofrequency loop heater may be used for heating the melt bonding materials. Such a machine is available from Magnaforce, Incorporated and sold under the name and model Heatstation 1500. Another such machine is available from Cath-Tip, Inc. and is sold under the model and name Cath-Tip II. There is a rise dwell and cool down time for the process. The total rise time is approximately 20 seconds and dwell time is approximately 10 seconds. During the dwell time the temperature is approximately 600° F. In one embodiment where nylon or PEBA are used, heating is at about 400° F., with dwell time of about 10 seconds.

Figure 8:
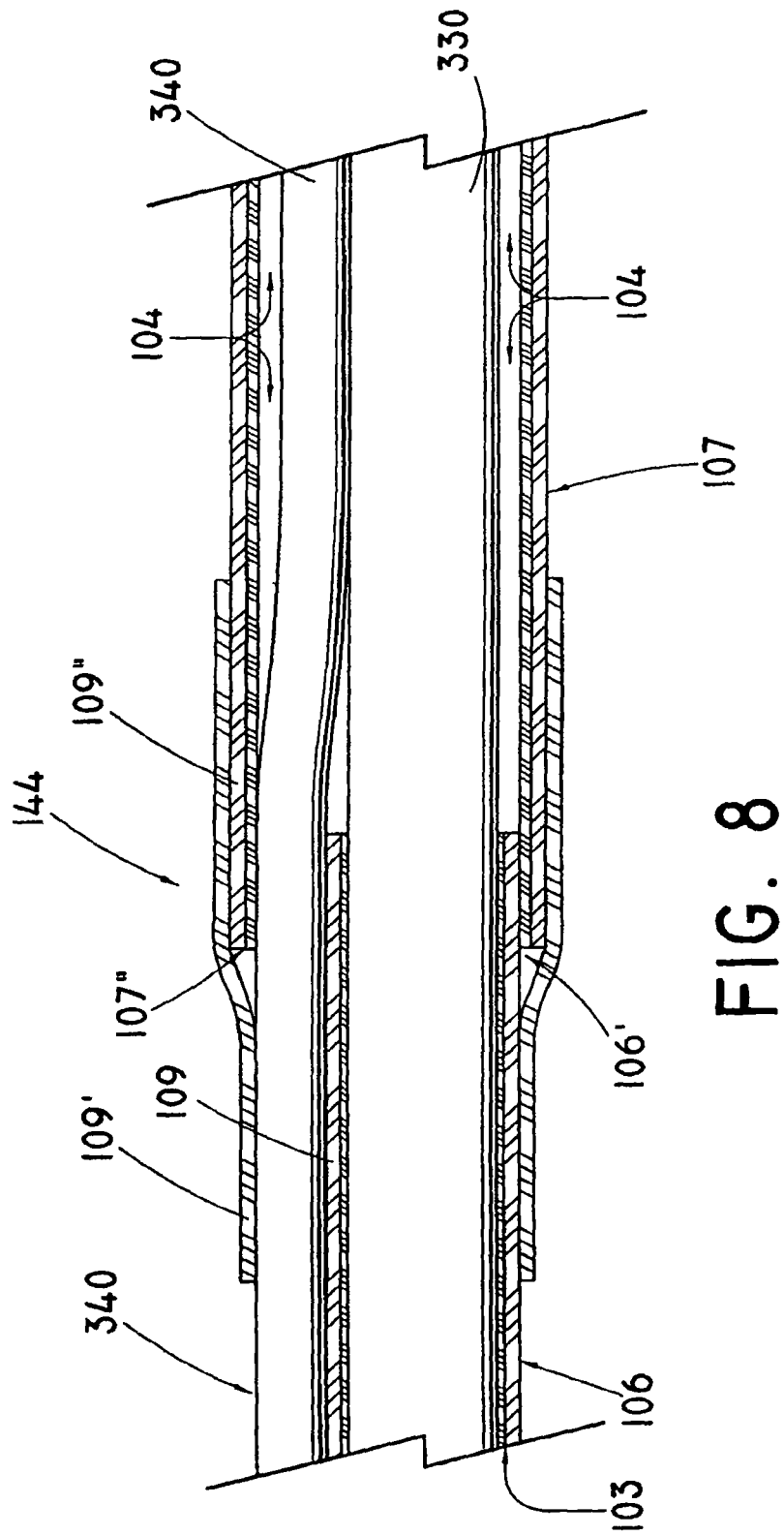
FIG. 8 illustrates a perspective sectional side view, broken away, of an outer sleeve body, a first sheath, and a second sheath before melt bonding, according to one embodiment of the invention.
Figure 11:
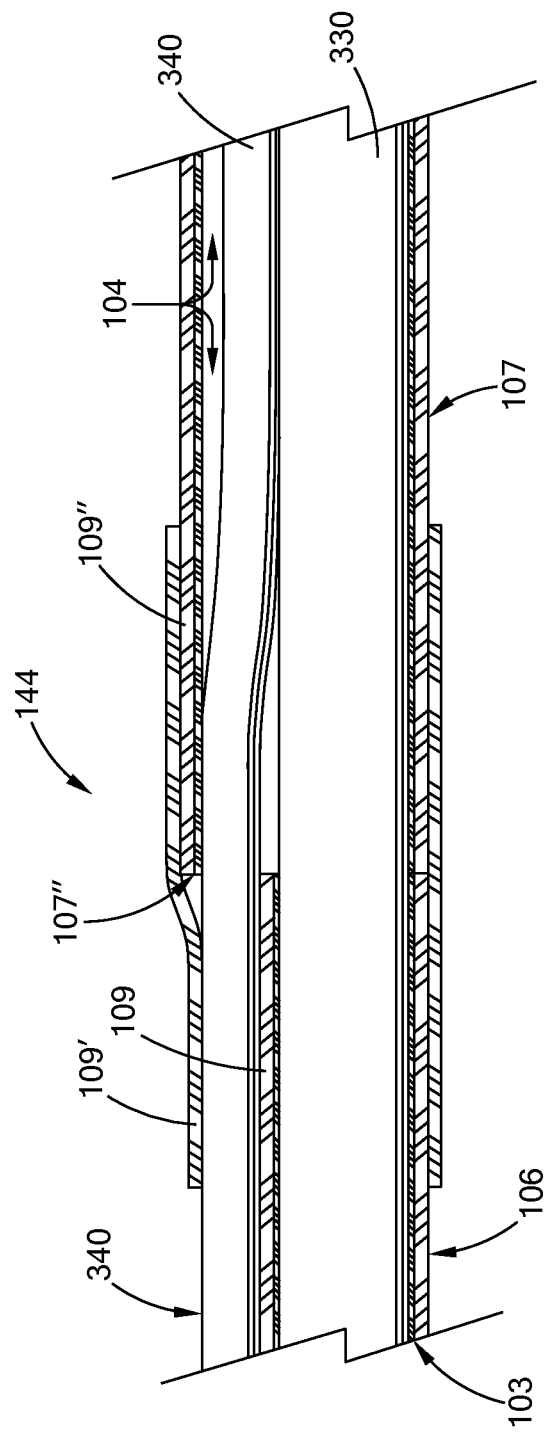
FIG. 11 illustrates a perspective sectional side view, broken away, of a joint assembly operatively coupling an outer sheath and an outer guide channel member, according to another embodiment of the invention.

FIGS. 8 and 11 illustrate a perspective sectional side view, broken away, of an outer sleeve body 144, a first sheath 106, and a second sheath 107. FIGS. 8 and 11 are intended to illustrate, by way of example only and not by way of limitation, one step before melt bonding, according to two embodiments of the invention.

In FIG. 8, the first sheath 106 is shown having a distal end portion 106' partially inserted (e.g., from 0.5 mm to about 10.0 mm, and in one embodiment about 3.0 mm) within a channel 104 of the second sheath 107. In FIG. 11, the first sheath 106 is shown having a distal end portion 106' positioned end-to-end with the a proximal end portion 107" of the second sheath 107. A first mandrel 330 positioned within a passageway 103 of the first sheath and the channel 104 of the second sheath 107. A second mandrel 340 is positioned on an outer layer 109 of the first sheath 106 and within the second sheath channel 104. The outer sleeve body 144 is disposed about a portion of the first sheath distal end portion 106', a portion of the second mandrel 340, and the proximal end portion 107" of the second sheath 107.

The outer sleeve body 144 comprises melt bonding material 109', the first sheath distal end portion 106' comprises an outer layer 109 comprising melt bonding material, and the second sheath proximal end portion 107" comprises an outer layer 109" comprising melt bonding material. In describing embodiments according to the invention in FIGS. 8 through 10G, it should be noted that an outer layer comprising melt bonding material does not foreclose the possibility that the outer layer is in actuality the only layer of a component, whether that component is a first sheath, second sheath, outer sleeve body or any portion thereof, a first sheath that comprises an outer sheath 50 discussed herein, and/or a second sheath that comprises an outer guide channel member 80 discussed herein.

As taught below, shrink-wrap material is disposed about the outer sleeve body 144. The shrink-wrap material constricts outer sleeve body 144. Heat is applied to cause melting of the outer sleeve melt bonding material 109', the first sheath distal end portion outer layer 109 of melt bonding material, and the second sheath proximal end portion outer layer 109" of melt bonding material. Upon cooling, the melt bonding materials form a solid state bond comprising a joint assembly 140 (FIG. 8A), the mandrels are removed, and the shrink-wrap material removed.

Figure 8A:
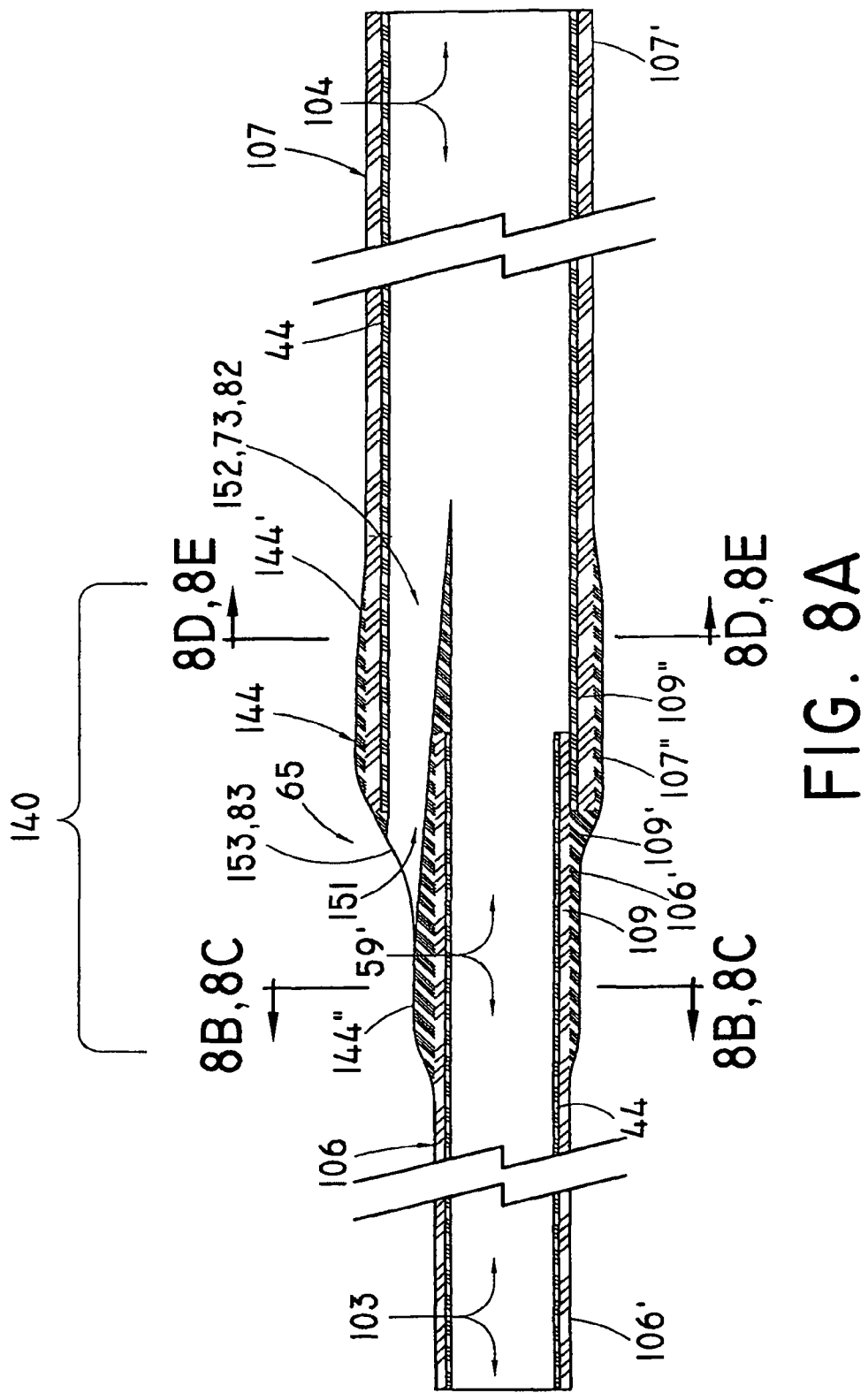
FIG. 8A illustrates a perspective sectional side view, broken away, of the joint assembly operatively coupling a first sheath and a second sheath after melt bonding, according to one embodiment of the invention.

FIG. 8A shows a schematic longitudinally section side view of one illustrative embodiment of a joint assembly 140 according to the invention prior to melt bonding for melt bonding an first sheath 106 and a second sheath 107. The first sheath 106 comprises a distal end portion 106' and a proximal end portion 106" and a passageway 103 therebetween, wherein the distal end portion 106' comprises an outer layer 109 comprising melt bonding material(s) and an optional inner layer 44 such as Teflon and like materials. The second sheath 107 comprises a distal end portion 107' and a proximal end portion 107" and a channel 104 therebetween, wherein the proximal end portion 107" comprises an outer layer 109" comprising melt bonding material(s) and an optional inner layer 44 such as Teflon and like materials. Optionally, the first sheath distal end portion 106' may be inserted partially within the second sheath channel 104.

The joint assembly 140 further comprises an outer sleeve body 144 intermediate a distal engaging portion 144' and a proximal engaging portion 144" defining a first channel 151 and/or a second channel 59' therebetween. The outer sleeve body distal engaging portion 144' and proximal engaging portion 144" comprise melt bonding material(s) 109'. The outer sleeve body distal engaging portion 144' disposes about and operatively couples to the second sheath outer layer 109" by melt bonding. The outer sleeve body proximal engaging portion 144" disposes about and operatively couples to the first sheath outer layer 109 by melt bonding. Otherwise stated, in one embodiment, the outer sleeve body distal engaging portion 144' and the second sheath outer layer 109" are melt bonded together, and the outer sleeve body proximal engaging portion 144" and the first sheath outer layer 109 are melt bonded together.

The first channel 151 is in fluid communication with the second sheath channel 104. The outer sleeve first channel 151 is sized for receiving a wire guide and functions to guide a wire guide, catheter, or other medical device out through the distal portion 13 at or near the breech position opening 65 with relatively little kinking, bending, buckling, or bowing. The optional second channel 59' is in fluid communication with the outer sheath passageway 59 and sized for receiving an inner compression member (an inner compression member receiving channel). It should be understood, however, that these are exemplary channels in a preferred embodiment intended to be used with a delivery system for self-expanding devices such as stents. In other words, in another embodiment the first channel 151 could be configured for receiving a catheter, cannula, or other medical device, tool, instrument, apparatus, or component used with the invention. Likewise, the second channel 59' may be configured for receiving a catheter, cannula, or other medical device, tool, instrument, apparatus, or component used with the invention.

Figure 8C:
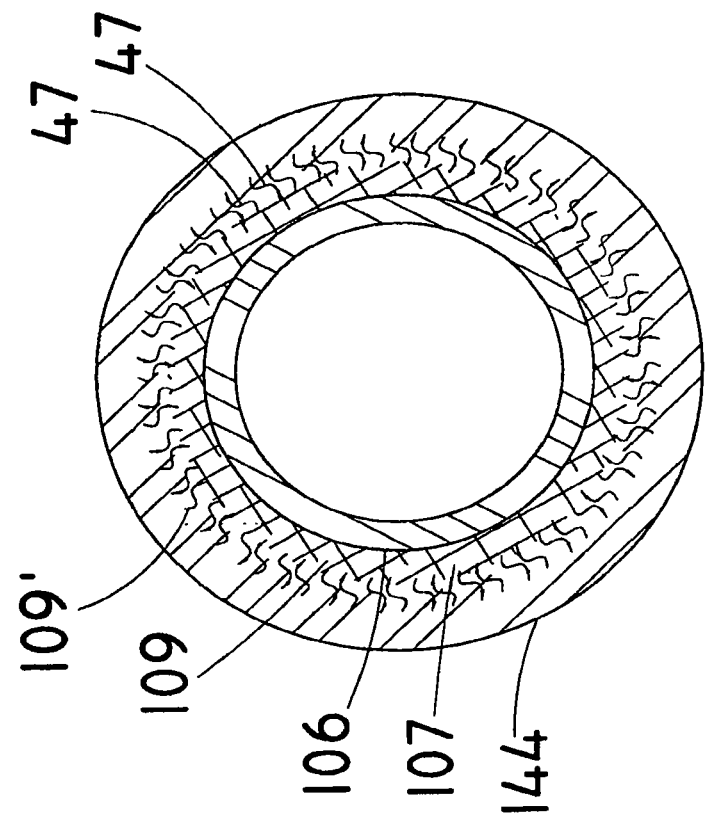

FIGS. 8A, 8B, 8C, and 8D present schematic representations of cross sections taken along the lines 8A-8A, 8B-8B, 8C-8C, and 8D-8D, respectively, of FIG. 8. More particularly, FIG. 8A shows the first sheath outer layer 109 and the melt bonding material 109' of the outer sleeve body proximal engaging portion 144" before melt bonding. Likewise, FIG. 8C shows the second sheath outer layer 109" and the melt bonding material 109' of the outer sleeve body distal engaging portion 144' before melt bonding. While all components are shown having interfaces in abutting physical contact, they need only be close enough to form a melt bond therebetween. By way of example, as previously explained in connection with the Flexor® sheath's outer layer 42 and inner layer 44, there may even be a middle layer comprising a coil 43 having spacings 43' through which the melt bonding material of the outer layer 42 may move to be into contact with the inner layer 44.

Figure 8B:
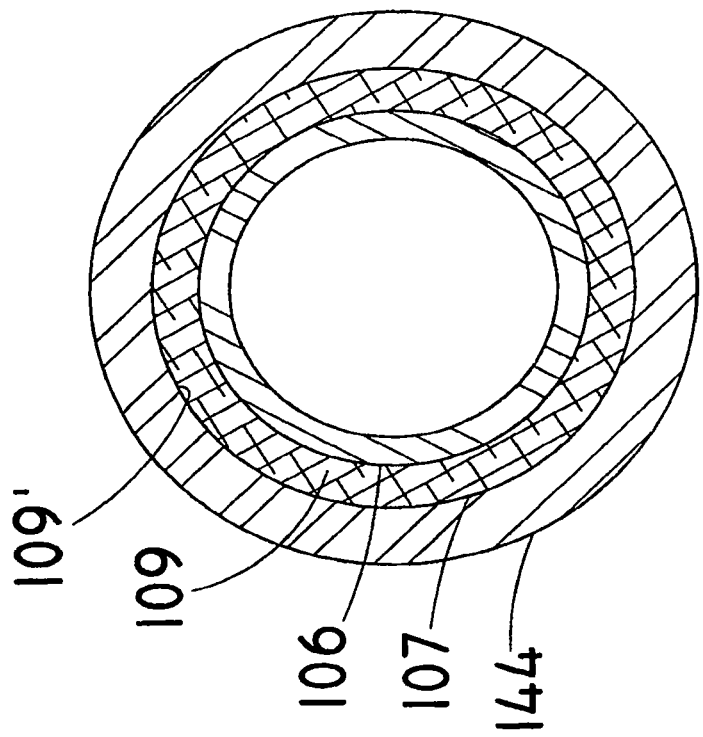

FIG. 8B shows the first sheath outer layer 109 and the melt bonding material 109' of the outer sleeve body proximal engaging portion 144" in one embodiment after melt bonding and forming a melt bond 47 at the interface. It should be noted that the first sheath outer layer 109 and the melt bonding material 109' of the outer sleeve body proximal engaging portion 144" could also be represented as though they completely liquefied and became miscible. Likewise, FIG. 8D shows the second sheath outer layer 109" and the melt bonding material 109' of the outer sleeve body distal engaging portion 144' after melt bonding and forming a melt bond 47 at the interface. Again, it should be noted that the second sheath outer layer 109" and the melt bonding material 109' of the outer sleeve body outer distal engaging portion 144' could also be represented as though they completely liquefied and became miscible.

FIGS. 8B and 8D further shows that the first and second melt bonding materials 109, 109', respectively, of the middle component 107 and the outer component 108 or other components that have been melt bonded, upon cooling to solid state will form a melt bond 47 operatively coupling the components and/or the melt bonding materials that comprise the components. This results in additional strength and helps to form a more solid connection to the melt bonded components, because a solid-state bond results from using a suitable form of heat for melting and solidifying (e.g., fusing and/or cross-linking bonds formed at the melt bonded material interfaces).

The joint assembly 140 thereby allows the physician to move the first and second sheaths 106, 107, respectively, substantially in unison (e.g., moving the first sheath 106 proximally results in proximal movement of the second sheath 107). When the first sheath 106 comprises an outer sheath 50 and the second sheath 107 comprises an outer guide channel member 80 according to one embodiment of the invention (e.g., FIGS. 4, 5, 6, 7), then the joint assembly 140 thereby allows the physician to move the outer guide channel member 80 relative to the inner guide channel member 70 while keeping the inner compression member 41, inner guide channel member 70, and stent 17 stationary or relatively stationary compared to the outer guide channel member 80 and outer sheath 50. The optional inner layer 44 if used in the second sheath 107 or outer guide channel member 80 help during storage as well as deployment as previously explained.

Figure 9:
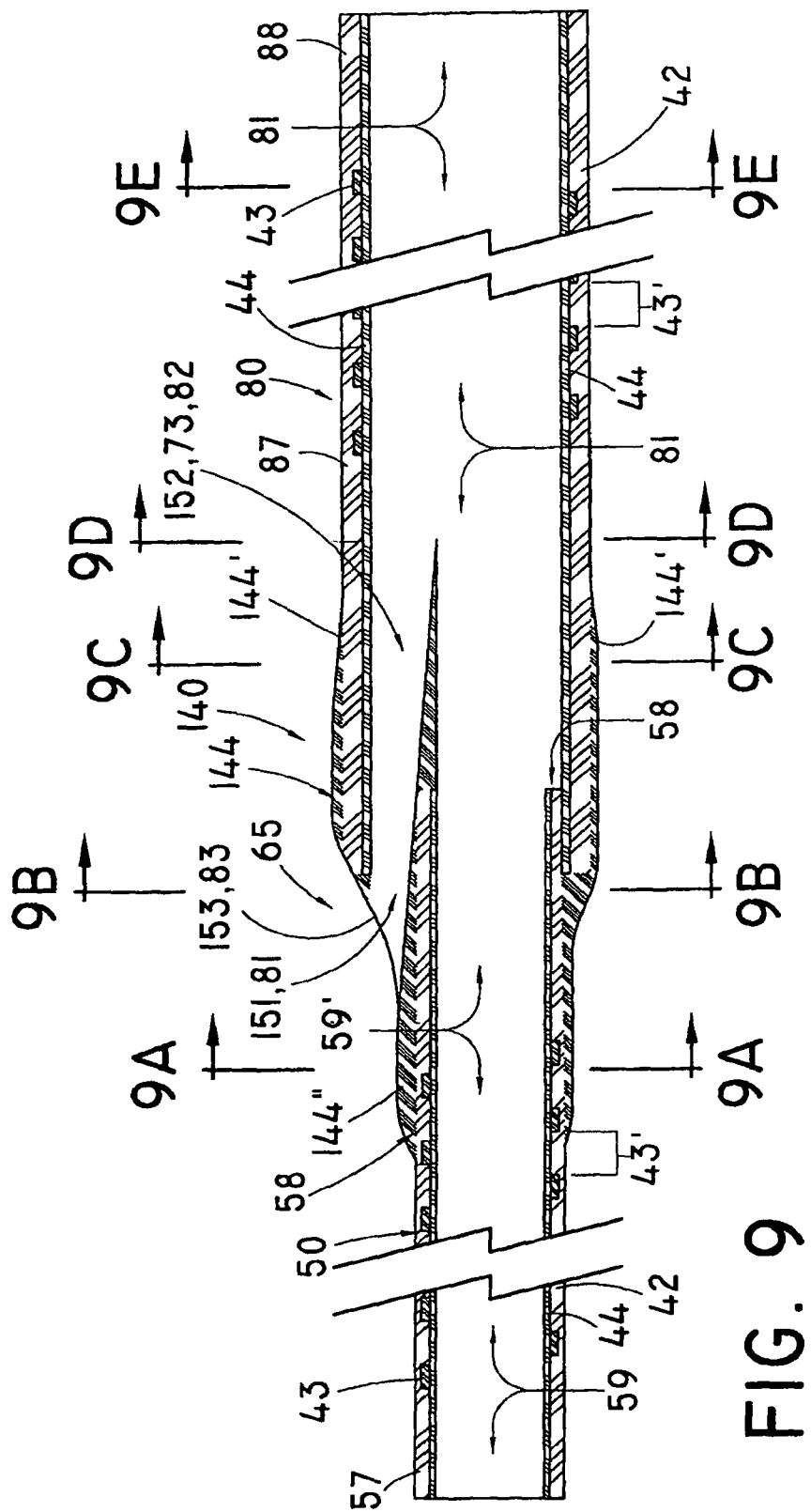
FIG. 9 illustrates a perspective sectional side view, broken away, of a joint assembly operatively coupling an outer sheath and an outer guide channel member, according to one embodiment of the invention.

FIG. 9 shows another embodiment of the invention comprising an outer sheath 50 of the middle section delivery device 14 and an outer guide channel member 80 of the distal portion 13 that optionally comprise separate units, whereby the outer sleeve body 144 operatively couples the outer sheath 50 and the outer guide channel member 80. The outer sheath 50 comprises a distal end portion 58 and a proximal end portion 57 and defining a passageway 59 therebetween (e.g., FIGS. 2C, 4, 5, 6, 7). The outer guide channel member 80 comprises a distal end portion 88 and a proximal end portion 87 and defining a guide channel 81 therebetween (e.g., FIGS. 4, 5, 6, 7). The joint assembly 140 further comprises an outer sleeve body 144 having and outer sleeve body distal engaging portion 144' melt bonded to the outer layer 42 of the outer guide channel member proximal end portion 86 and having an outer sleeve body proximal engaging portion 144" melt bonded to the outer layer 42 of the outer sheath distal end portion 58. [[Otherwise stated, in one embodiment, the outer sleeve body distal engaging portion 144' and the outer guide channel member proximal end portion 86 are melt bonded together, and the outer sleeve body proximal engaging portion 144" and the outer sheath distal end portion 58 are melt bonded together. The outer sleeve body 144 further comprises a first channel 151 and an optional second channel 59' defined by the outer sleeve body distal and proximal engaging portions 144', 144", respectively.

The outer sheath distal end portion 58 is positioned longitudinally "at or near" the outer guide channel member proximal end portion 87', where the phrase "at or near" is used to describe these components being longitudinally at, within, or a short distance of each other. For example, in one embodiment the outer sheath distal end portion 58 and the outer guide channel member proximal end portion 87' are spaced longitudinally apart from 0.5 mm to about 5.0 mm. In another embodiment, the outer sheath distal end portion 58 and the outer guide channel member proximal end portion 87' could make indirect contact—as with intervening parts—and be operatively coupled by the outer sleeve body 144. In another embodiment, the outer sheath distal end portion 58 and the outer guide channel member proximal end portion 87' are touching end-to-end, in direct contact, abutting, or overlapping. In a preferred embodiment, the outer sheath distal end portion 58 is approximately 13.0 mm in length, of which the distal 3.0 mm is inserted within the outer guide channel member second end portion 87'. The melt-bonded outer sleeve body 144 disposes about 6.0 mm of the proximal length of the outer guide channel member second end portion 87' and disposes about 10.0 mm of the distal length of the outer sheath distal end portion 58 which 10.0 mm extends proximally from the outer guide channel member second end portion 87'. In these embodiments, the outer sleeve body 144 has a distal engaging portion 144' operatively coupled to the outer guide channel member proximal end portion 87' and has a proximal engaging portion 144" operatively coupled to the outer sheath distal end portion 58.

FIG. 9 also shows that optionally, in one embodiment, Flexor® sheaths may be used for the outer sheath 50, the outer guide channel member 80, or both. In one embodiment, the outer guide channel member 80 may be a Flexor® sheath approximately 5 French in diameter and the outer sheath 50 may be a Flexor® sheath approximately 4 French in diameter, wherein a melt-bonded outer sleeve body 144 operatively couples the two Flexor® sheaths.

More particularly, the outer sheath 50 may comprise an inner layer 44 and passageway 59 extend longitudinally therethrough, and a middle layer comprising the coil 43 that forms a turn or turns longitudinally disposed about the inner layer 44 and spacings 43' between the turns. The coil 43 optionally discontinues proximal to the outer sheath distal end portion 58 and distal to the outer sheath proximal end portion 57. The outer layer 42 is longitudinally disposed about the coil 43 and melt bonded to the inner layer 44 through the coil spacings 43. The proximal end portion 144" of the melt-bonded outer sleeve body 144 disposes about at least a portion of the outer layer 42 of the outer sheath distal end portion 58 and melt bonds thereto, while the outer sleeve body distal engaging portion 144' melt bonds the outer layer 42 of the outer guide channel member second end portion 87.

Furthermore, the outer guide channel member 80 may comprise an inner layer 44 and channel 81 extending longitudinally therethrough, and a middle layer comprising a coil 43 that forms a turn or turns longitudinally disposed about the inner layer 44 and spacings 43' between the turns. The coil 43 optionally discontinues proximal to the outer guide channel member distal end portion 88 and distal to the proximal end portion 87. The outer layer 42 is longitudinally disposed about the coil 43 and melt bonded to the inner layer 44 through the coil spacings 43. The distal engaging portion 144' of the melt-bonded outer sleeve body 144 disposes about at least a portion of the outer layer 42 of the outer guide channel member proximal end portion 87 and melt bonds thereto, while the outer sleeve body proximal engaging portion 144" is disposed about and melt bonds to the outer layer 42 of the outer sheath distal end portion 58. Stated otherwise, in one embodiment, the distal engaging portion 144' of the outer sleeve body 144 and the outer layer 42 of the outer guide channel member proximal end portion 87 are melt bonded together, while the outer sleeve body proximal engaging portion 144" and the outer layer 42 of the outer sheath distal end portion 58 are melt bonded together.

It may be desirable to have a longer outer sleeve proximal end portion 144" relative to the outer sleeve distal engaging portion 144'. In one embodiment, the distal end portion 144' of the melt-bonded outer sleeve body 144 disposes about (the phrase "disposes about" describes embodiments of enveloping, surrounding, wrapping around, covering, overlaying, superposed over, encasing, ensheathing, and the like) the outer member second end portion 87 for a length of about 1.0 mm to about 15.0 mm, and in another embodiment disposes about 5.0 mm to about 10.0 mm of the outer guide channel member second end portion 87 in order to have adequate surface contact with the outer guide channel member second end portion outer layer 42. Meanwhile, the outer sleeve body proximal engaging portion 144" disposes about the outer sheath distal portion 58 for a length of about 2.0 mm to about 20.0 mm, and in another embodiment disposes about 7.0 mm to about 15.0 mm of the outer sheath distal portion 58 in order to have adequate surface contact with the outer sheath distal portion 58. In a preferred embodiment, the melt-bonded joint 140 has a outer sleeve body distal engaging portion 144' that is approximately 6.0 mm and overlaps approximately 6.0 mm of the outer guide channel member second end portion 87, while the outer sleeve body proximal engaging portion 144" is approximately 10.0 mm and overlaps approximately 10.0 mm of the outer sheath distal portion 58, wherein 10.0 mm extends proximally from a 3.0 mm tip portion that has been inserted within the channel 81 of the outer guide channel member second portion 87.

As taught above, the joint assembly 140 will provide appropriate structural integrity, reinforcement, and bonding properties. The joint assembly 140 may comprise melt-bonding material identified above, and in an exemplary embodiment comprises a polyether block amide, nylon, and/or a nylon natural tubing. Moreover, the joint assembly 140, when used to operatively couple an outer sheath 50 and outer guide channel member 80, provides strength by adding material and reshaping the outer layers 42 at or near the outer guide channel member second end portion 87 and the outer sheath distal end portion 58. In addition, the outer sleeve body 144 is intermediate the outer sleeve body distal engaging portion 144' and an outer sleeve body proximal engaging portion 144", may be approximately tubular, and houses the first channel 151 in fluid communication with the guide channel 81 of the inner guide channel member 80 and further houses an optional second channel 59' in fluid communication with the. The outer sleeve body first channel 151 functions to guide a wire guide, catheter, or other medical device out through the distal portion 13 at or near the breech position opening 65 with relatively little kinking, bending, buckling, or bowing.

In FIGS. 8 and 9 for use with the medical device delivery system according to the invention (FIGS. 1, 2, 4, 5, 6, 7), the joint assembly 140 further comprises a joint entry port 152 at or near the outer sleeve body distal engaging portion 144' and a joint exit port 153 at or near the outer sleeve body proximal engaging portion 144", wherein joint entry port 152 and joint exit port 153 define the first channel 141 of the joint assembly 140. The first channel 141 is sized such that a wire guide 16 may move proximally through the inner member guide channel 71 of the inner guide channel member 70 of the medical device delivery system (FIGS. 1, 2, 4, 5, 6, 7) and may egress proximally from the inner member exit port 73 of the inner guide channel member 70, wherein the proximal passage of the inner guide channel member exit port 73 is designated as the joint entry port 152 in this embodiment.

Optionally, the joint entry port 152, joint exit port 153, and first channel 141 may be coterminous with entry port 82, exit port 83, and guide channel 81 of the outer guide channel member 80. In other words, a wire guide 16 moves proximally through the inner member guide channel 71 and egresses from the inner member exit port 73, wherein the proximal passage of the inner member exit port 73 is designated as the outer member wire guide entry port 82 (as well as the joint exit port 153) in that embodiment. Likewise, the wire guide 16 may egress proximally out the outer member exit port 83, wherein the exit port 83 is designated as the joint exit port 153 of the joint assembly 140.

The joint assembly 140 may further define an optional second channel 59' between the engaging ends 144', 144". The channel 59' may be configured for receiving an inner compression member 41 extending through the passageway in the outer sheath 50. In the embodiment illustrated in FIG. 9, the second channel 59' and the first channel 141 are coextensive for a portion of the joint 140 between the engaging ends 144', 144".

FIGS. 9A-9E are cross sectional views of FIG. 9 taken along the lines A-A, B-B, C-C, D-D, and E-E. For clarity, the outer layers 44 of the outer sheath 50 and the outer guide channel member 80 and the outer sleeve body 144 are shown in layers. It should be understood, however, that after melt bonding they may be depicted as one uniform cross section, respectively.

FIG. 9A is a cross sectional view of the outer sheath 50. Moving from the center in the outward direction, this cross section has a second channel 59', an inner layer 44, and a coil 43, whereby an outer layer 42 and an outer sleeve body proximal engaging portion 144" are melt bonded. The outer sleeve body exit port 153 and outer guide channel member exit port 83 are also shown coterminous, as is the outer guide channel member 80. The outer sheath 50 has a smaller diameter, such as approximately 4 French, compared to the diameter of the outer guide channel member member 80, which may be approximately 5 French.

FIG. 9B is a cross sectional view of the joint assembly at the outer sleeve body proximal engaging portion 144". As shown therein, the joint assembly comprises an inner layer 44, an outer sleeve body first channel 151, and guide channel 81 of the outer guide channel member 80, whereby the outer sleeve body 144 and the outer layer 42 of the outer sheath 50 are melt bonded.

FIG. 9C shows the joint assembly at a location showing the outer sleeve body distal and proximal engaging portions 144'. By comparison, it can be seen that the outer sleeve body first channel 141 is coterminous with the guide channel 81 of the outer guide channel member 80 and converge distally. Also shown are the inner layer 44 and guide channel 81 of the outer guide channel member 80. In other words, and as will be explained below, the stainless steel mandrels that are utilized to form these respective channels are converged during the manufacturing process by tapering the outer sheath 50 at or near an outer sheath distal end portion 58.

FIG. 9D shows the joint assembly at the outer guide channel member engaging 80. By comparison to FIG. 8C, and as will be explained below, the stainless steel mandrels that are utilized to form the respective channels are converged (and abutted) during the manufacturing process at the cross section shown along the lines 9D-9D. As a result, the outer sleeve body first channel 151 and the guide channel 81 form a "figure-8 shape" with the guide channel 81 forming the lower loop and the channels 151, 81 being coterminous at the upper loop. Also shown is an outer layer 42 of the outer guide channel member 80.

FIG. 9E is a cross sectional view of the outer guide channel member 80 having a guide channel 81, coil 43, inner layer 44, and outer layer 42. The guide channel 81 would be in fluid communication with outer sleeve body first and second channels 151, 59' of the joint assembly 140. The term "fluid communication" and variants thereof are not used lexicographically but instead are used to describe embodiments of the invention such that the channels 81, 151, and 59' are configured to receive a wire guide, catheter, cannula, and/or other medical device, tool, instrument, apparatus, or component used with the invention.

The joint assembly 140 may vary in length as desired. The length depends on the desired surface contact with the outer guide channel member 80 and/or the outer sheath 50. In one embodiment, the joint assembly 140 has a length from approximately 5.0 mm to approximately 25.0 mm. In another embodiment, the joint 140 is from approximately 10.0 mm to approximately 20.0 mm. In still another embodiment, the joint 140 is approximately 16.0 mm.

Alternatively and/or in addition to a melt-bond 47, the joint assembly 140 may utilize glue, adhesives, resins, welding (laser, spot, etc.), soldering, brazing, adhesives, chemical bonding materials or combinations thereof to secure the outer sheath 50 and outer guide channel member 80, respectively. Optionally and/or in addition to the foregoing means for operatively coupling, the joint assembly 140 may use a wedge effect, a press-fit-tight configuration, a crimp sleeve, a surface roughness (e.g., sandblasting, etching, knurling, grinding, etc.) on a surface of the outer sheath 50, the outer guide channel member 80, or the joint assembly 140 for increasing bonding, a tongue and groove joint, interlocking protrusion and indentation, a wire, an internal screw thread, an external screw thread, and/or other mechanically, chemically, and/or chemical-mechanically means and/or any combination thereof by which the outer sleeve body 144, outer sheath 50, and/or outer guide channel member 80 are bonded, joined, adjoined, connected, associated, united, mated, interlocked, conjoined, fastened, held together, clamped, and crimped.

Method for Operatively Coupling the Outer Sheath and the Outer Guide Channel Member Methods of manufacturing and of joining a first sheath and a second sheath for a medical device, such as a medical device for delivering a self-expanding stent, prosthetic valve device, and other implantable articles inside a patient's body are also provided. For illustration purposes, the method will be described using an outer sheath 50 as the first sheath and using an outer guide channel member 80 as the second sheath.

FIGS. 10A through 10G show steps in a method 300 providing a melt-bonded joint assembly 140 (FIG. 10G) for joining an outer sheath 50 at or near an outer sheath distal end portion 58 and an proximal second end portion 87 of an outer guide channel member 80 at a transition region 60 (see FIGS. 4, 5, 6, 7). For clarity and emphasis of the step in the successive figures, reference numbers may be repeated in the description but not shown in the figures but readily shown in a preceding FIG. 10A through 10G or other figure described above. The joint assembly joins the distal end portion 58 and second end portion 87, in a way that provides a breech position as described above, with a thermal mechanical melt bond that cures relatively fast and uniformly to distribute the stress across the entire bond and provide uniform flexibility.

Figure 10A:
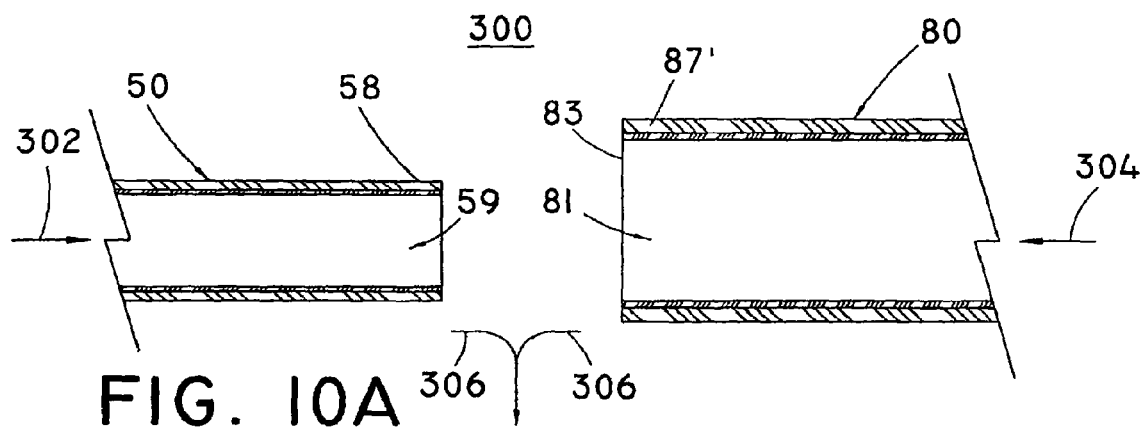
FIGS. 10A through 10G are schematic diagrams illustrating a method of bonding an outer sheath distal end and the outer guide channel member second end for use in a delivery system configured for rapid insertion delivery of self-expanding devices.

In FIG. 10A, an outer sheath 50 is provided (step 302). This figure illustrates a schematic view, broken away, of an outer sheath 50 according to an embodiment of the invention described above. The outer sheath 50 is a flexible, elongate (long) tubular assembly having a length of approximately 100 cm to approximately 125 cm, though it may be longer or shorter as needed. The outer sheath 50 includes a passageway 59 configured for receiving an elongate inner compression member 41 (not shown). At the outer sheath distal end portion 58, the inner diameter of the passageway 59 is about 0.032 inches and the outer diameter is about 0.050 inches, although these diameters may vary. In one embodiment, the outer sheath 50 is a Flexor® sheath.

Also in FIG. 10A, an outer guide channel member 80 is provided (step 304). This figure illustrates a schematic view, broken away, of an outer guide channel member 80 according to an embodiment of the invention described above. The outer guide channel member 80 is generally tubular and comprises a wire guide entry port 82 at a first end portion 88 and a proximal wire guide exit port 83 located at or near the second end portion 87' (e.g., FIGS. 4, 5, 6, 7). The ports 82, 83 define an outer member guide channel 81 therebetween for receiving a wire guide and/or an inner guide channel member 70 (e.g., FIGS. 4, 5, 6, 7). The outer guide channel member 80 may vary in length from about 10 to 40 cm, and in one embodiment is approximately 25 cm in length. In one embodiment, the inner diameter of the channel 81 is about 0.053 inches and the outer diameter is about 0.068 inches, although these diameters may vary. In one embodiment, the outer guide channel member 80 is a Flexor® sheath.

Figure 10B:
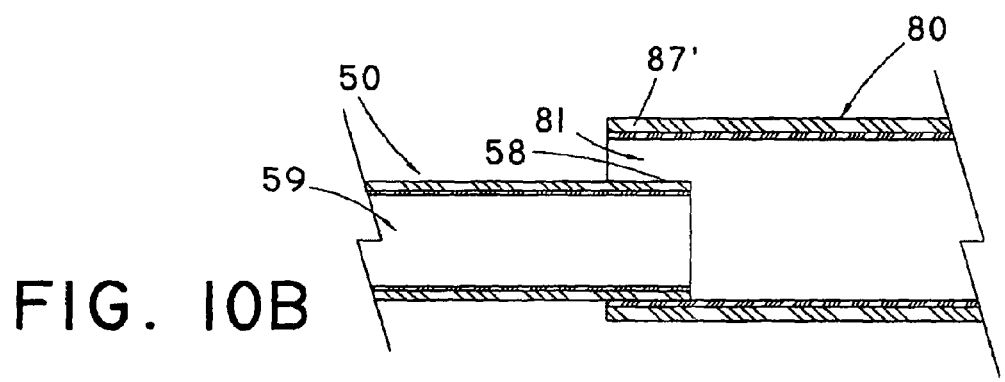

In FIG. 10B, the outer sheath distal end portion 58 and an outer guide channel member second end portion 87' are conjoined (step 306). In a preferred embodiment a portion (e.g., 3.0 mm) of the outer sheath distal end portion 58 is inserted into a channel 81 of the outer member second end portion 87' as described above. While the distal end portion 58 is inserted into the channel 81 in the preferred embodiment, it could also straddle the outer member second end portion 87'. For example, a portion of the end portion 87' may extend into the outer sheath channel 59 while a portion of the distal end portion 58 may extend into the channel 81 and outside the proximal end portion 87'. Otherwise stated, conjoined describes any embodiment whereby the outer sheath distal end portion 58 and an outer guide channel member second end portion 87' touch, meet, come substantially close to touching and meeting in an end-to-end or overlapping arrangement.

Figure 10C:
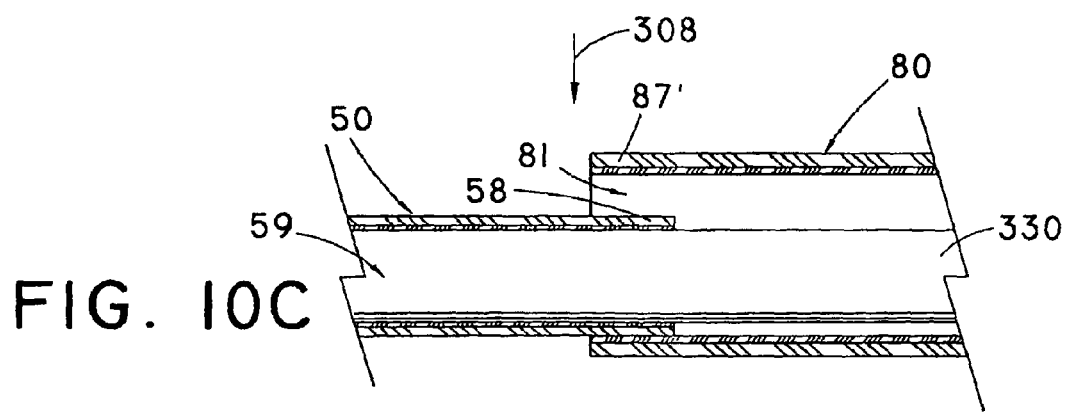

FIG. 10C shows a first mandrel 330 positioned (step 308) within the outer sheath passageway 59 and the guide channel 81 of the outer guide channel member 80. In one embodiment, the mandrel 330 is a stainless steel mandrel having a Teflon coating and a diameter approximately 0.028 inches. The mandrel 330 extends distally approximately 10 cm from the distal opening 89 of the outer guide channel member first end portion 88 to permit the mandrel 330 to be secured during manufacturing, handling, removing, and the like. Optionally, where the device will include an atraumatic tip 170 (FIG. 4, 5, 6, 7), the mandrel 330 would be positioned (step 308) within the guide channel 171 and would extend distally approximately 10 cm out the wire guide entry port 172 of the distal first end portion 178 (FIG. 4, 5, 6, 7).

Figure 10D:
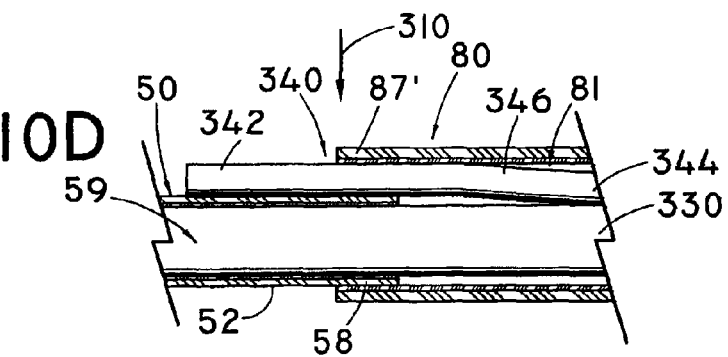

In FIG. 10D, a second mandrel 340 is positioned (step 310) on a joint engaging outer surface 52 of the outer sheath distal end portion 58 and within the guide channel 81 of the outer guide channel member 80. In one embodiment, the mandrel 340 is a stainless steel mandrel having a Teflon coating. More particularly, the mandrel 340 has a proximal end 342 that runs proximally along the outside surface 52 of the outer sheath distal end portion 58, a distal end 344 within the outer member guide channel 81, and a middle portion 346 configured with a bend, or being flexible so that it can bend, to make the transition from the outer surface 52 to the guide channel 81. In one embodiment, the mandrel 340 is Teflon coated and has a diameter of approximately 0.025 inches. The mandrel 340 may be any desired length to permit the mandrel 340 to be secured during manufacturing, handling, removing, and the like.

Figure 10E:
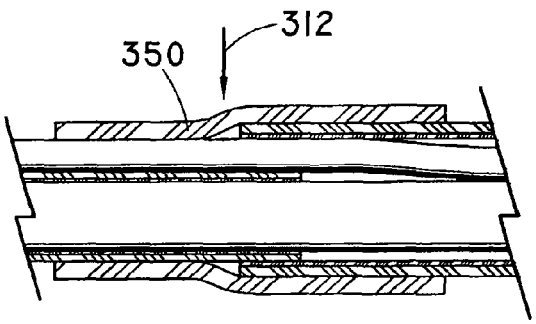

FIG. 10E shows a melt-bonding material 350, for example, comprising a polyether block amide, nylon, and/or a nylon natural tubing or other melt-bonding material described above (individually and collectively, "PEBA" and/or "nylon"), being disposed (step 312) about a portion of the outer sheath distal end portion 58 and outer member second end portion 87'. The material 350 may be any suitable configuration, length, and diameter, and in one embodiment is tubular and has a length of approximately 10.0 mm, an inner diameter of approximately 0.065 inches, an outer diameter of approximately 0.0745 inches, and a wall thickness approximately 0.0045 inches. The material 350 may be disposed (step 312) in any fashion or means for joining the outer member second end portion 87' and outer sheath distal end portion 58. For example, material 350 may be disposed (step 312) by being slipped, pulled, stretched, applied, or rolled over the second end portion 87' and distal end portion 58. The material 350 need not be disposed (step 312) evenly over the outer member second end portion 87' and outer sheath distal end portion 58. For example, in one embodiment the material 330 is disposed (step 312) over approximately 3.0 mm of the outer member second end portion 87' and approximately 7.0 mm of the outer sheath distal end portion 58 so as to melt bond together the outer member second end portion 87' and outer sheath distal end portion 58.

Figure 10F:
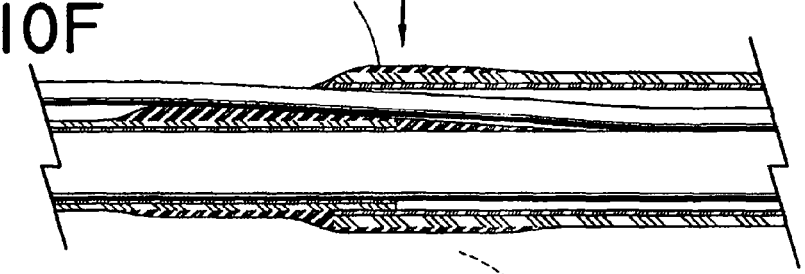

In FIG. 10F, a shrink-wrap material 360 comprising a polymer such as, for example, a non-radiopaque floatenated ethylene propylene shrink tubing ("NFEPS"), is disposed (step 314) about the melt-bonding material 350, a portion of the outer sheath distal end portion 58, and a portion of the outer member second end portion 87. The shrink-wrap material 360 may also be any laminating, taping, wrapping (thermally fusing together), painting and curing, and the like suitable for holding the melt-bonding material 350, a portion of the outer sheath distal end portion 58, and a portion of the outer member second end portion 87' while heat is applied to the assembly so as to melt, directly or indirectly, the melt-bonding material 350. Moreover, the shrink-wrap material 360 may be any suitable configuration, length, and diameter. In one embodiment that is tubular, the material 360 has a length of approximately 3.0 cm, an inner diameter of approximately 0.083 inches, an outer diameter of approximately 0.101 inches, and a wall thickness approximately 0.009 inches. The material 360 may be disposed (step 314) in any fashion or means for joining the outer member second end portion 87' and outer sheath distal end portion 58. By way of example and not by way of limitation, material 350 may be disposed (step 312) by being slipped, pulled, stretched, applied, wrapped, painted, taped, or rolled over the second end portion 87' and distal end portion 58.

FIG. 10F also shows the step whereby the melt-bonding material 350 is melted (step 316). As used to describe an embodiment of the invention, the melting 316 step is any means for heating, melting, liquefying, softening, fusing, or making malleable, pliant, supple, moldable, ductile, or otherwise penetrable by the melt-bonding material 350 in the region defined by the shrink-wrap material 360 and melt-bonding material 350. Such a machine is available from Magnaforce, Incorporated and sold under the name and model Heatstation 1500. Another such machine is available from Cath-Tip, Inc. and is sold under the model and name Cath-Tip II. In one embodiment, two semi-circular jaws clamp onto (and heat) the shrink-wrap material 360 and melt-bonding material 350 at about 410° F. for about 10 seconds.

The temperature, total rise time, and dwell time will vary depending on many factors including, for instance, the actual melt-bonding material 350 and shrink-wrap material 360 used. For instance, materials have different "melt bonding" temperatures at which the material will soften and become almost tacky without substantial degradation. In one embodiment where PEEK tubing is used, because PEEK melts at about 633° F., the PEEK tubing may be heated from about 628° F. to about 638° F. There is a rise dwell and cool down time for the process. The total rise time is approximately 20 seconds and dwell time is approximately 10 seconds. During the dwell time the temperature is approximately 600 F.

The melting step 316 causes the shrink-wrap material to constrict and the material 350 to soften and melt about portions of the mandrels 330, 340, the outer sheath distal end portion 58, and the outer member second end portion 87. Then, cooling (step 318) the melt-bonding material 350 (see FIG. 9F). The cooling step 318 allows the region defined by the shrink-wrap material 360 and melt-bonding material 350 to return to room temperature or some other desired temperature, thereby causing the melt-bonding material 350 to return to solid state (e.g., become solid, again), thereby forming a melt-bonded joint 140 described above.

Figure 10G:
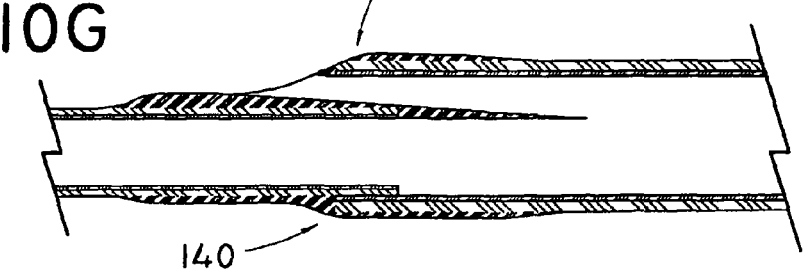

In FIG. 10G, the shrink-wrap material 360 is then removed (step 320) by any suitable means, such as by cutting, pealing, shaving, and the like by any suitable means, including but not limited to a blade, laser, splicer, and cutting device.

The above-described method of manufacturing need not be performed sequentially. For instance, in method 300, an outer guide channel member 80 may be provided (step 304) before the outer sheath 50 is provided (step 302). Similarly, the mandrel 340 may be positioned (step 340) before the mandrel 330 is positioned (step 330). These are only two of the examples illustrating a non-sequential method of manufacturing according to the invention.

It is intended that the foregoing detailed description of a melt-bonded joint for bonding sheaths, catheters, and tubular devices for use with a medical device delivery system and medical devices, and methods of manufacturing the melt-bonded joint be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

While particular elements, embodiments, and applications of the present invention have been shown and described, it will be understood, of course, that the invention is not limited thereto since modifications may be made by those skilled in the art, particularly in light of the foregoing teachings. Therefore, it is therefore contemplated by the appended claims to cover such modifications as incorporate those features which come within the spirit and scope of the invention.

What is claimed is:

1. A joint assembly of a rapid insertion catheter delivery system, comprising:
    an outer sleeve body comprising a melt bonding material and operatively coupling a distal end portion of a first tube having a first length to a proximal end portion of a second tube having a second length, the outer sleeve body having a length smaller than the first length and the second length, the first tube comprising a first passageway and the second tube comprising a second passageway in fluid communication with the first passageway, wherein the first tube has a first diameter and the second tube has a second diameter larger than the first diameter, and wherein each of the first tube and the second tube includes an outer layer comprising a melt bonding material, the melt bonding materials of the first and second tubes being melt bonded to the melt bonding material of the outer sleeve body, the joint assembly thereby comprising a melt bond at an interface between the melt bonding material of the outer sleeve body and the melt bonding materials of the first and second tubes, the melt bond extending along the length of the outer sleeve body, and wherein the outer sleeve body comprises an exit passageway in fluid communication with the second passageway for guiding a medical device out of the joint assembly without kinking or bending.

2. The joint assembly of claim 1 wherein the distal end portion of the first tube and the proximal end portion of the second tube are positioned end-to-end without overlap, the outer sleeve body overlapping the distal end portion of the first tube and the proximal end portion of the second tube.

3. The joint assembly of claim 1 wherein the first tube further comprises:
- an inner layer underlying the outer layer of the first tube; and
- a coil disposed between the inner layer and the outer layer, the coil extending along at least a portion of a length of the first tube in a spiral configuration,
- wherein the outer layer comprising the melt bonding material is melt bonded to the inner layer through spacings between turns of the coil.

4. The joint assembly of claim 1 wherein the second tube further comprises:
- an inner layer underlying the outer layer of the second tube; and
- a coil disposed between the inner layer and the outer layer, the coil extending along at least a portion of a length of the first tube in a spiral configuration,
- wherein the outer layer comprising the melt bonding material is melt bonded to the inner layer through spacings between turns of the coil.

5. The joint assembly of claim 1 wherein the exit passageway extends from the second passageway to an exit port in the outer sleeve body, the exit port comprising a breech position opening.

6. The joint assembly of claim 1 wherein the first tube is an outer sheath of the rapid insertion catheter delivery system.

7. The joint assembly of claim 1 wherein the second tube is an outer guide channel member of the rapid insertion catheter delivery system.

8. The joint assembly of claim 1 wherein the melt-bonding materials of the outer sleeve body, the first tube, and the second tube are selected from the group consisting of nylon, nylon natural tubing, polyether block amide, polyetheretherketone, thermoplastic, thermosetting plastic, resin, polypropylene, polyethylene, polyester, polyamide, ionomer, polycarbonate, polyphenylene oxide, polyphenylene sulphide, acrylic, liquid crystal polymer, polyolefin, polyethylene acrylate acid, polyvinylidene fluoride, polyvinyl, polyvinyl chloride, and polytetrafluorethylene.

9. The joint assembly of claim 1, wherein the melt-bonding materials of the outer sleeve body, the first tube, and the second tube are the same.

10. The joint assembly of claim 1, wherein at least one of the melt-bonding materials of the outer sleeve body, the first tube, and the second tube is different from the others.

11. The joint assembly of claim 1 further comprising the rapid insertion catheter delivery system, the system comprising a proximal portion having a handle operatively coupling a proximal end portion of the first tube, wherein the first tube extends at least about 50.0 cm from the handle to the outer sleeve body.

12. The joint assembly of claim 11 further comprising an elongate inner compression member having a proximal end disposed within the proximal portion of the rapid insertion catheter delivery system and having a distal mating end portion operatively coupled to an inner guide channel member slideably received within the second tube.

13. The joint assembly of claim 12 wherein the inner guide channel member comprises a first end portion having an entry port and a second end portion having an exit port and defining a guide channel therebetween, a proximal stent restraint being located intermediate the first and second end portions, and a stent platform being intermediate the proximal stent restraint and the inner guide channel member stent entry port.

\* \* \* \* \*